US012746598B2

(12) United States Patent
Das et al.

(10) Patent No.: US 12,746,598 B2
(45) Date of Patent: Sep. 29, 2026

(54) BIMETALLIC FLUORESCENT NANOCOMPOSITES FOR CANCER THERANOSTICS

(71) Applicant: COUNCIL OF SCIENTIFIC AND INDUSTRIAL RESEARCH, New Delhi (IN)

(72) Inventors: Sourav Das, Telangana (IN); Sudip Mukherjee, Telangana (IN); Chitta Ranjan Patra, Telangana (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 985 days.

(21) Appl. No.: 17/909,239

(22) PCT Filed: Mar. 5, 2021

(86) PCT No.: PCT/IN2021/050215
§ 371 (c)(1),
(2) Date: Sep. 2, 2022

(87) PCT Pub. No.: WO2021/176480
PCT Pub. Date: Sep. 10, 2021

(65) Prior Publication Data

US 2023/0086363 A1 Mar. 23, 2023

(30) Foreign Application Priority Data

Mar. 6, 2020 (IN) ............................ 202011009670

(51) Int. Cl.

| | |
|---|---|
| ***A61K 47/64*** | (2017.01) |
| ***A61K 49/00*** | (2006.01) |
| ***A61P 35/00*** | (2006.01) |
| ***B22F 1/054*** | (2022.01) |
| ***B22F 1/102*** | (2022.01) |
| ***B22F 1/17*** | (2022.01) |
| ***B22F 9/24*** | (2006.01) |
| ***B82Y 30/00*** | (2011.01) |

(52) U.S. Cl.
CPC ................ *B22F 9/24* (2013.01); *A61K 47/64* (2017.08); *A61K 49/0019* (2013.01); *A61K 49/0056* (2013.01); *A61K 49/0065* (2013.01); *A61P 35/00* (2018.01); *B22F 1/056* (2022.01); *B22F 1/102* (2022.01); *B22F 1/17* (2022.01); *B82Y 30/00* (2013.01)

(58) Field of Classification Search
CPC .......... A61K 9/00; A61K 9/0093; A61K 9/14; A61K 49/0057
See application file for complete search history.

(56) References Cited

U.S. PATENT DOCUMENTS

2013/0034854 A1 * 2/2013 Ashworth-Sharpe ....................... C07F 9/65522 977/920

OTHER PUBLICATIONS

Pang et al (Lysozyme-stabilized bimetallic gold/silver nanoclusters as a turn-on fluorescent probe for determination of ascorbic acid and acid phosphatase, Anal Methods, 2017, 9, 6713-6718) (Year: 2017).*
Dutta et al (Bimetallic silver nanoparticle-gold nanoparticle nanocluster embedded composite nanoparticles for cancer theranostics, Journal of Materials Chemistry B, 4, 793-800, 2016 (Year: 2016).*
International Search Report mailed May 27, 2021 in reference to co-pending Application No. PCT/IN2021/050215 filed Mar. 5, 2021.
Written Opinion mailed May 27, 2021 in reference to co-pending Application No. PCT/IN2021/050215 filed Mar. 5, 2021.
Touyz, "Molecular and cellular mechanisms in vascular injury in hypertension: role of angiotensin II", Editorial Review, Current Opinion in Nephrology and Hypertension, vol. 14, pp. 125-131, 2005.
Kumari, et al., "Reactive Oxygen Species: A Key Constituent in Cancer Survival", Biomarker Insights, vol. 13, pp. 1-9, 2018.
Lisanti, et al., "Hydrogen peroxide fuels aging, inflammation, cancer metabolism and metastasis", Cell Cycle, vol. 10, Issue 15, pp. 2440-2449.
Kim, et al., "ROS homeostasis and metabolism: a critical liaison for cancer therapy", Experimental & Molecular Medicine, vol. 48, pp. 1-13, 2016.
D'Autréaux, et al., "ROS as signalling molecules: mechanisms that generate specificity in ROS homeostasis", Molecular Cell Biology, vol. 8, pp. 813-824, Oct. 2007.
Franco, et al., "Oxidative stress, DNA methylation and carcinogenesis", Cancer Letters, vol. 266, pp. 6-11, 2008.
Irani, et al., "Mitogenic Signaling Mediated by Oxidants in Ras-Transformed Fibroblasts", Science, vol. 275, pp. 1649-1652, Mar. 14, 1997.
Renschler, The emerging role of reactive oxygen species in cancer therapy, European Journal of Cancer, vol. 40, pp. 1934-1940, 2004.
Storz, "Reactive Oxygen Species in Tumor Progression", Frontiers in Bioscience, vol. 10, pp. 1881-1896, May 1, 2005.
Chanock, et al., "The Respiratory Burst Oxidase", The Journal of Biological Chemistry, vol. 269, No. 40, pp. 24519-24522, Oct. 7, 1994.

(Continued)

*Primary Examiner* — Micah Paul Young
(74) *Attorney, Agent, or Firm* — DINSMORE & SHOHL LLP

(57) ABSTRACT

Fluorescent bimetallic nanocomposites ($M_1$@$M_2$-NCs) of silver-gold (Ag@Au-NC) and silver-platinum (Ag@Pt-NC) are prepared by reducing silver nitrate ($AgNO_3$) on gold nanoparticles (AuNPs) and platinum nanoparticles (PtNPs) using sodium borohydride ($NaBH_4$) at alkaline pH=11, in the presence of a lysozyme that acts as a template, and in the presence of a capping and stabilizing agent. The biocompatible bimetallic nanocomposites ($M_1$@$M_2$-NCs) have promising multifunctional applications (cell imaging, biosensing, therapeutics) observed by both in vitro as well as in vivo experiments. The fluorescent bimetallic nanocomposites ($M_1$@$M_2$-NCs) of silver-gold (Ag@Au-NC) and silver-platinum (Ag@Pt-NC) may be useful as an alternative nanomedicine in cancer theranostics applications.

15 Claims, 25 Drawing Sheets

(56) References Cited

OTHER PUBLICATIONS

You, et al., "Reactive oxygen species mediated theranostics using a Fenton reaction activable lipo-polymersome", Journal of Materials Chemistry B, vol. 7, pp. 314-323, 2019.
Tabish, et al., "Developing the next generation of graphene-based platforms for cancer therapeutics: The potential role of reactive oxygen species", Redox Biology, vol. 15, pp. 34-40, 2018.
Wang, et al., "Superoxide dismutases: Dual roles in controlling ROS damage and regulating ROS signaling", Journal of Cell Biology, vol. 217, No. 6, pp. 1915-1928, 2018.
Bohunicky, et al., "Biosensors: the new wave in cancer diagnosis", Nanotechnology, Science and Applications, vol. 11, pp. 1-10, 2011.
Oh, et al., "Fluorescent Polymer Nanoparticle for Selective Sensing of Intracellular Hydrogen Peroxide", ACS Nano, pp. A-I, 2011.
Paravicini, et al., "NADPH Oxidases, Reactive Oxygen Species, and Hypertension", Diabetes Care, vol. 31, Supplement 2, pp. S170-S180, Feb. 2008.
Wei, et al., "Simple synthesis of thioglycolic acid-coated CdTe quantum dots as probes for Norfloxacin lactate detection", Journal of Luminescence, vol. 161, pp. 47-53, 2015.
Wan, et al., "Highly-sensitive colorimetric detection of $H_2O_2$ based on the Pt@Te nanorods", Physica E., vol. 69, pp. 207-211, 2015.
Zhang, et al., "Fluorescent gold nanoclusters based photoelectrochemical sensors for detection for $H_2O_2$ and glucose", Biosensors and Bioelectronics, vol. 67, pp. 296-302, 2015.
Katurji, et al., "Approaches and Methods to Measure Oxidative Stress in Clinical Samples: Research Applications in the Cancer Field", Oxidative Medicine and Cellular Longevity, pp. 1-30, 2019.
Ventola, "The Nanomedicine Revolution Part 2: Current and Future Clinical Applications", vol. 37, No. 10, pp. 582-592, 2012.
Shameli, et al., "Synthesis and characterization of silver/talc nanocomposites using the wet chemical reduction method", International Journal of Nanomedicine, vol. 5, pp. 743-751, 2010.
Correia, et al., "Development of bio-hybrid piezoresistive nanocomposites using silk-elastin protein copolymers", Composites Science and Technology, vol. 172, pp. 134-142, 2019.
Chen, et al., "Synthesis of a novel graphene-based gold nanocomposite using PVEIM-b-PNIPAM as a stabilizer and its thermosensitivty for the catalytic reduction of 4-nitrophenol", Inorganic Chemistry, pp. 1-11, 2019.
Tee, "Nanomedicine and Nanotechnology in Health Care", J. Nanomed Nanotechnol, vol. 7, No. 4, p. 1, 2016.
Ramkumar, et al., "Synthesis of platinum nanoparticles using seaweed *Padina gymnospora* and their catalytic activity as PVP/PtNPs nanocomposite towards biological applications", ScienceDirect, vol. 92, pp. 479-490, 2017.
Elahi, et al., "Recent biomedical applications of gold nanoparticles: A review", Talanta, https://doi.org/10.1016/j.talanta.2018.02.088.

* cited by examiner

BIMETALLIC FLUORESCENT NANOCOMPOSITES FOR CANCER THERANOSTICS

CROSS REFERENCES TO RELATED APPLICATIONS

This application is a national-stage application under 35 U.S.C. § 371 of International Application No. PCT/IN2021/050215, filed Mar. 5, 2021, which International Application claims benefit of priority to Indian Patent Application No. 202011009670, filed Mar. 6, 2020.

TECHNICAL FIELD

The present disclosure relates to a fluorescent bimetallic nanocomposites ($M_1@M_2$-NCs) of a silver-gold (Ag@Au-NC) and a silver-platinum (Ag@Pt-NC) by reducing a silver nitrate ($AgNO_3$) on a gold nanoparticles (AuNPs) and a platinum nanoparticles (PtNPs) using sodium borohydride ($NaBH_4$) at alkaline pH=11, in presence of a lysozyme that acts as a template, capping and stabilizing agent. Particularly, the present disclosure relates to biocompatible bimetallic nanocomposites ($M_1@M_2$-NCs) having promising multifunctional applications as in cell imaging, bio-sensing, therapeutics and the same is observed by both in vitro as well as in vivo experiments. More particularly, the present disclosure relates to fluorescent bimetallic nanocomposites ($M_1@M_2$-NCs) of silver-gold (Ag@Au-NC) and silver-platinum (Ag@Pt-NC) useful as an alternative nanomedicine in cancer theranostics applications.

BACKGROUND

Reactive oxygen species (ROS) has been the byproduct of metabolism occurring in the cellular level and it has multi-functional roles in various cellular processes [Touyz et al. Current Opinion in Nephrology and Hypertension, 2005, 14, 125-131]. There is an uncanny relationship between ROS and the cancer cells [Kumari et al., 2018, Biomarker Insights, 13, 1177271918755391]. Cancer cells show very high levels of reactive oxygen species (ROS) that help them to persuade the surrounding cells to become glycolytic. The presence of excess $H_2O_2$ instigates oxidative stress to the nearby cells which gives fuel to the cancer cells for their growth and survivability [Lisanti et al., Cell Cycle, 10, 2440-2449]. The overall changes in the balance of these redox substances and malfunctioning in the pathways of the redox reactions leads to uncontrolled growth of the cells and leads to cancer [Kim et al., 2016, Experimental & Molecular Medicine, 48, e269]. Subsequently, it assists the carcinogenic cells to effectively permeate through the blood channels initiating tumor growth and cell damage.

Generally, ROS are chemically reactive molecules derived from molecular oxygen that constantly produced as a natural byproduct in response to normal metabolism (in humans). [D'Autréaux et al., 2007, Nature Reviews Molecular Cell Biology, 8, 813]. However, the successive generation of exogenous or endogenous ROS under certain conditions of oxidative stress can damage the cellular integrity (rupture of DNA, proteins, lipids etc.) which frequently contributes to carcinogenesis [Franco et al., Cancer Letters, 266, 6-11]. This change from normal to oncogenic form is attributed to overall genetic, metabolic and environmental changes which results in elevated levels of ROS generation [Kim et al., 2016, Experimental & Molecular Medicine, 48, e269]. On the other hand, ROS reduce the proliferation of cancer cells by increasing the oxidative stress [Irani et al., 1997, Science, 275, 1649-1652; Renschler et al., 2004. European Journal of Cancer, 40, 1934-1940]. Hence, ROS acts as a double-edged sword. When ROS is induced by macrophages inside the tumor region by the help of a certain stimuli such as TNF-α, it results in death of the tumor cells [Storz et al., 2005, Front Bioscience, 10, 1881-1896]. These in turn activates a series of events leading to conversion of superoxide into hydrogen peroxide mainly under the influence of NADPH oxidase. This leads to apoptosis of the tumor cells [Chanock et al., 1994, Journal of Biological Chemistry, 270, 24519-24519]. Recently, You et al., showed the ROS induced apoptosis towards the cancer cells. The ROS was generated by Fenton reaction that results in the killing of the cancer cells [You et al., 2019, Journal of Materials Chemistry B, 7, 314-323]. Tabish et al., explained the role of ROS in cancer theranostics using the graphene based nanoplatforms. The authors showed the generation of oxidative stress due to interaction of graphene with cells [Tabish et al., 2018, Redox biology, 15, 34-40]. These published reports support the importance of ROS and their role towards cancer theranostics applications.

Among ROS, $H_2O_2$ is the most common form of ROS present in the living system. The formation of $H_2O_2$ from the ROS takes place within the mitochondria itself under the influence of superoxide dismutase [Wang et al., 2018, The Journal of Cell Biology, 217, 1915-1928]. The quantitative estimation of the $H_2O_2$ in the cellular level can be effectively utilized to diagnose various diseases like cancer [Bohunicky et al., 2011, Nanotechnology, Science and Applications, 4, p. 1]. Notably, the diagnosis of ROS including $H_2O_2$ is mainly hindered due to their short life time and low detectable concentrations [Oh et al., 2012, ACS Nano, 6, 8516-8524]. However, the lifespan of $H_2O_2$ is little greater than other components of ROS [Paravicini et al. Diabetes Care, 2008, 31(Supplement 2), S170-S180]. Conventional methods for the detection of $H_2O_2$ (HPLC detection, colorimetric detection, analytical detection, automated fluorometric method, enzymatic methods, non-enzymatic methods, photometric detection and derivatization techniques) lack in effectiveness due to their complexity, low detection limit, large number of critical steps and longer response time [Wei et al., 2015, Journal of Luminescence, 161, 47-53; Wan et al., 2015, Physica E: Low-dimensional Systems and Nanostructures, 69, 207-211; Zhang et al., 2015, Biosensors and Bioelectronics, 67, 296-302]. Biomarkers present within the cells are also being exploited to detect the disease status within the affected person. But here also the variation in the amount of the data has led to difficulty in drawing a conclusion of the disease [Katerji et al., 2019, Oxidative Medicine and Cellular Longevity, 2019, 29 pages]. Hence, to tackle the above mentioned problems in detection of ROS and $H_2O_2$, scientists are using new technologies and methods to improve the therapeutic and diagnostics. With the rapid growth of various nanomedicines in the field of cancer theranostics, design and development of alternative multi-functional NCs is urgently required for the detection of $H_2O_2$ and cancer treatment [Ventola et al., 2012. Pharmacy and Therapeutics, 37, 512].

Over the past few decades, the wet chemistry methods including the reduction method of the precursor renders fruitful development of the nanocomposite materials [Shameli et al., 2010, International Journal of Nanomedicine, 5, 743-751]. Various scientists all over the world have been synthesizing different nanocomposites using proteins [Correia et al., 2019, Composites Science and Technology, 172, 134-142], stabilizers [Chen et al, 2019, Inorganic Chemistry Frontiers, 6, 903-913]. Also, there is an increased interest observed in the making of the noble metal nanocomposites owing to their tunable properties, chemical and biological sensing properties, and optical properties. Earlier reports suggest that these noble metals (Au, Ag and Pt) were doped or deposited in order to use them in photocatalytic reaction [Correia et al., 2019, Composites Science and Technology, 172, 134-142]. Recently, these noble metals have found immense attention in the field of biological applications [Elahi et al., 2018. Talanta, 184, 537-556; Adam et al., 2016, Journal of Nanomedicine Nanotechnology, 2016, 7, 4; Rajkumar et al., 2017, Biomedicine and Pharmacotherapy, 92, 479-490].

In this context, we designed and developed silver coated lysozyme-templated two different bimetallic nanocomposites (NCs) Ag@Au-NC and Ag@Pt-NC by in situ reduction of $AgNO_3$ on gold (AuNPs) and platinum (PtNPs) nanoparticles. These NCs were cytotoxic in various cancer cells as discussed in the upcoming sections but biocompatible in normal cells. The NCs demonstrated strong green fluorescence that was used as cellular imaging. The $H_2O_2$ sensing was carried out in both the in vitro conditions as well as in cellular level using the green fluorescence enhancement experiments. The present disclosure provides new designs of fluorescent based NCs that significantly inhibited the cancer cell proliferation in vitro and reduced tumor growth in vivo in subcutaneous melanoma tumor model. Altogether, the present disclosure supports the future applications of both the nanocomposites as an alternative nanomedicine for various biomedical applications (cellular imaging, $H_2O_2$ sensor and cancer therapy).

A main object of the present disclosure is to provide fluorescent bimetallic nanocomposites ($M_1$@$M_2$-NCs) of silver-gold and silver-platinum (Ag@Au-NC and Ag@Pt-NC).

Another objective of the present disclosure is to show the cell imaging ability of the nanocomposites.

Yet another objective of the present disclosure is to show the effective in vitro as well as in vivo (C57/BL6 melanoma tumor model) anti-cancer efficacy of the NCs itself without any anti-cancer drugs.

Yet another objective of the present disclosure is to analyse the sensing activity of the NCs towards the hydrogen peroxide ($H_2O_2$).

Yet another objective of the present disclosure is to provide biocompatible, stable fluorescent bimetallic nanocomposites useful for multifunctional applications such as cell imaging, bio-sensing and anti-cancer activity.

SUMMARY

Accordingly, present disclosure relates to a bimetallic nanocomposite (M1@M2-NC) comprising:

i. a metal $M_1$ as an outer-layer of the nanocomposite;

ii. a metal $M_2$ as an inner metallic layer of the nanocomposite; and iii. a capping agent;

wherein, the metal $M_1$ is selected from the group consisting of silver, chromium, manganese, iron, cobalt, nickel, copper, zinc, magnesium and calcium;

the metal $M_2$ is metal nanoparticle selected from the group consisting of gold, platinum, copper, chromium, magnesium, calcium, palladium, manganese, cobalt, nickel, titanium, zinc, cerium, iron and thallium;

the capping agent is selected from the group consisting of lysozyme protein, casein, bovine serum albumin (BSA), lacto transferrin, insulin, horseradish peroxidase, collagen and pepsin; the lysozyme is a biocompatible globular protein.

In an embodiment of the present disclosure, a size of the nanocomposite is in the range of 100-300 nm and shape of the nanocomposite is spherical.

In another embodiment, present disclosure provides a process for the preparation of bimetallic nanocomposite comprising the steps of:

i. providing an aqueous solution of a metal $M_2$ salts;

ii. optionally adding an aqueous solution of a stabilizing agent;

iii. adding an aqueous solution of sodium borohydride ($NaBH_4$) at temperature in the range of 25 to 35° C. under stirring to obtain a reaction mixture of metal $M_2$ nanoparticles;

iv. adding an aqueous solution of metal $M_1$ salt to the reaction mixture as obtained in step (iii) at temperature in the range of 25 to 35° C. with stirring to obtain a reaction mixture;

v. adding an aqueous solution of capping agent to the reaction mixture as obtained in step (iv) to obtain a solution;

vi. adjusting pH of the solution as obtained in step (v) by adding an aqueous solution of sodium hydroxide (NaOH) between 9 to 11 followed by stirring for a time period in the range of 10 to 15 minutes at temperature in the range of 25 to 35° C. to obtain a solution;

vii. adding an aqueous solution of sodium borohydride to the solution as obtained in step (vi) at temperature in the range of 25 to 35° C. for a time period in the range of 6 hr to 8 hr with stirring to obtain nanocomposite solution;

viii. centrifuging the nanocomposite solution as obtained in step (vii) at speed in the range of 6000 to 10,000 rpm, at temperature in the range of 15 to 20° C. for a time period in the range of 20 to 30 minutes followed by washing with water to obtain the bimetallic nanocomposite.

In yet another embodiment of the present disclosure, the metal salt M1 is selected from the group consisting of nitrates of silver, chromium, manganese, iron, cobalt, nickel, copper, zinc, magnesium and calcium.

In yet another embodiment of the present disclosure, the metal salt M2 is selected from the group consisting of chlorides of gold, platinum, chromium, magnesium, calcium, copper, palladium, manganese, cobalt, nickel, titanium, zinc, cerium, iron and thallium.

In yet another embodiment of the present disclosure, stabilizing agent used is poly ethylene glycol.

In yet another embodiment of the present disclosure, the bimetallic nanocomposite exhibits green fluorescence useful for cancer cells imaging.

In yet another embodiment of the present disclosure, the nanocomposite exhibits hydrogen peroxide ($H_2O_2$) sensing application by fluorescence enhancement property inside cells in in vitro conditions ($1\text{-}10^{-9}$M).

In yet another embodiment of the present disclosure, the nanocomposite show cytotoxicity towards various cancer cells selected from B16F10, MDA-MB-231, MCF-7 and HeLa under in vitro conditions.

In yet another embodiment of the present disclosure, the nanocomposite utilizes $H_2O_2$ and reactive oxygen species (ROS) near tumor microenvironment to modulate its structure to release silver ions ($Ag^+$) that assist in killing cancer cell and display tumor regression in murine melanoma in vivo model.

BRIEF DESCRIPTION OF DRAWINGS

(FIG. 1B) X-ray diffraction (XRD) pattern of Ag@Au and Ag@Pt; (FIG. 1C) Size distribution by DLS of Ag@Au and Ag@Pt nanocomposites; (FIGS. 1D and 1E) FESEM images of the nanocomposites (FIG. 1D) Ag@Au, (FIG. 1E) Ag@Pt showing almost spherical nature of nanocomposites; (FIGS. 1F-1I) TEM images of synthesised (FIG. 1F) Ag@Au, (FIG. 1G) high magnification TEM of Ag@Au, (FIG. 1H) Ag@Pt, (FIG. 1I) high magnification TEM of Ag@Au; (FIG. 1J) XPS data of synthesized Ag@Au and Ag@Pt, respectively.

(FIGS. 8C and 8D) apoptosis analysis using the annexin V/propidium iodide (PI) in (FIG. 8C) MCF 7 cells and (FIG. 8D) B16F10 cells (FIG. 8E) silver ion release study from Ag@Au and Ag@Pt NCs in time dependent manner.

(FIG. 9B) body weight treated and untreated groups; (FIG. 9C) representative images of mice from the UT, Ag@Au and Ag@Pt groups; (FIG. 9D) tumor weight data of treated and untreated groups; (FIG. 9E) survival data for the tumor-bearing mice in treatment groups (Ag@Au and Ag@Pt) were also evaluated; (FIG. 9F) biodistribution of the Ag from Ag@Au and Ag@Pt in major organs and tumors.

(FIG. 15B) MCF 7 cells treated with Ag@Au, Ag@Au+TBHP, Ag@Pt and Ag@Pt+TBHP, (FIG. 15C) B16F10 cells treated with Ag@Au, Ag@Au+$H_2O_2$, Ag@Pt and Ag@Pt+$H_2O_2$; TTEST, *P" 0.05.

(FIG. 16B) fluorescence intensity is quantified using the Image J software.

PROCUREMENT DETAILS

Tetrachloroauric (III) acid ($HAuCl_4$, $3H_2O$), hexachloroplatinic acid ($H_2PtCl_6$), lysozyme (from chicken egg; Catalogue No. L6876-25G), sodium borohydride ($NaBH_4$), tert-Butyl hydroperoxide (TBHP), 3-(4,5-dimethylthiazol-2-yl)-2,5-diphenyl tetrazolium bromide (MTT) reagent, doxorubicin (DOX), $H_2O_2$ (30 wt. % in water), RNase A from bovine pancreas, RIPA buffer, propidium iodide (PI), Fluoroshield™ with DAPI, bis Benzimide H 33342 trihydrochloride (Hoechst), Hank's balanced salt solution (HBSS) buffer, tris buffered saline (TBS), Dulbecco's Modified Eagle Medium (DMEM), Dulbecco's Phosphate Buffer Saline (DPBS), penicillin, streptomycin, kanamycin, bovine serum albumin (BSA), trypsin (from bovine pancreas) and fetal bovine serum (FBS) were purchased from Sigma-Aldrich Chemicals, USA. Triton X-100 was obtained from Genetix Brand Asia Pvt. Ltd. (India). Tween-20 was procured from Amresco (USA). Silver nitrate ($AgNO_3$), methanol (MeOH), PVDF were purchased from Merck Specialities Pvt. Ltd. (India). Sodium hydroxide (NaOH), xylene, isopropanol were bought from Finar (India). Dimethyl sulfoxide (DMSO) was purchased from Rankem (India). Sodium bicarbonate ($NaHCO_3$), acrylamide, bis-acrylamide, glycine were obtained from HiMedia (India). EBM media was purchased from Lonza (USA). Milli-Q-grade water (18.2 MΩ·cm) was used for all of the experiments.

Cell lines: Cancer cell lines (B16F10: mouse melanoma cell line; MDA-MB-231: human breast cancer cell line) and normal cell line (CHO: Chinese hamster ovarian cell line) were purchased from the American Type Culture Collection (ATCC), USA. Cancer cell (MCF-7: human breast adenocarcinoma) was purchased from NCCS, Pune, India. Normal cell line (HUVEC: human umbilical vein endothelial cell line) was procured from Lonza, (USA). Human endothelial somatic hybrid cell lines (EA.hy926) were a kind gift from Steve Oglesbee, TCF, UNC Lineberger Comprehensive Cancer Center, NC, USA and Suvro Chatterjee, AU-KBC, Chennai, India.

For chick chorioallantotic membrane (CAM) assay, fertilized Chicken eggs were brought from Directorate of Poultry Research, Raj endra Nagar, Hyderabad.

Antibodies: Primary antibody (Ki-67 Primary (PA5-19462, Thermoscientific (USA); 1:100) and secondary antibody (goat anti-rabbit IgG-PE, sc-3739, Santa Cruz; (USA) 1:100) were used for immunofluorescence assay.

Kits: Annexin V-FITC-labeled apoptosis detection kit (Cat No #640914) was purchased from Biolegend. Tunel assay kit: APO-DIRECT™ (Cat no #51-6550AZ) was purchased from BD Biosciences, (San Jose, CA).

DETAILED DESCRIPTION

The present disclosure provides a facile synthesis of bimetallic fluorescent nanocomposites (Ag@Au and Ag@Pt NCs) using a 14.3 KDa protein lysozyme, abundant in body fluids. This present disclosure provides that the synthesis was carried out at pH=11 (adjusted by NaOH) using the $NaBH_4$ as a reducing agent.

Figure 18:
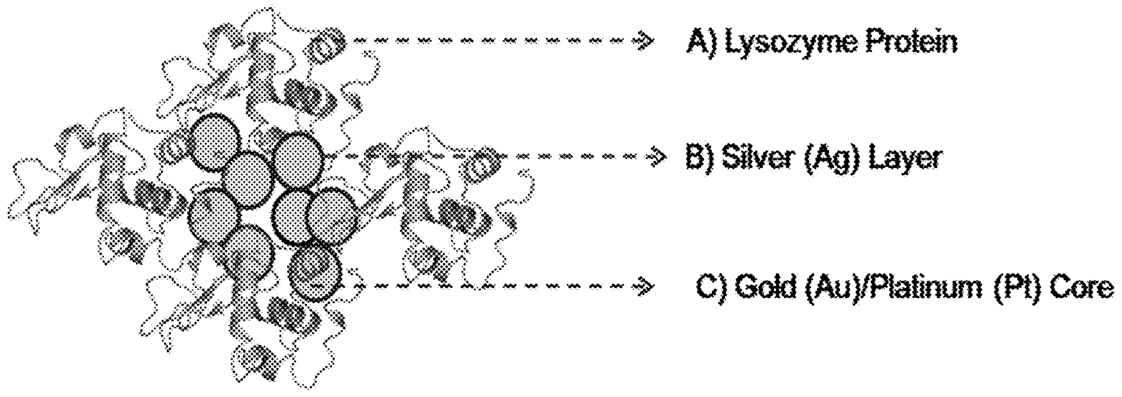
FIG. 18 represents schematic diagram of the nanocomposites (NCs).

The fluorescent bimetallic nanocomposites (NCs) of silver-gold (Ag@Au-NC) and silver-platinum (Ag@Pt-NC) was synthesized by reducing silver nitrate ($AgNO_3$) on gold nanoparticles (AuNPs) and platinum nanoparticles (PtNPs) using sodium borohydride ($NaBH_4$) at alkaline pH=11, in presence of lysozyme that acts as a template, capping and stabilizing agent (FIG. 18). A indicates the lysozyme protein; B indicates the silver (Ag) layer; C indicates the gold (Au) [for Ag@Au NC]/platinum (Pt) [for Ag@Pt NC] core.

Figure 19:
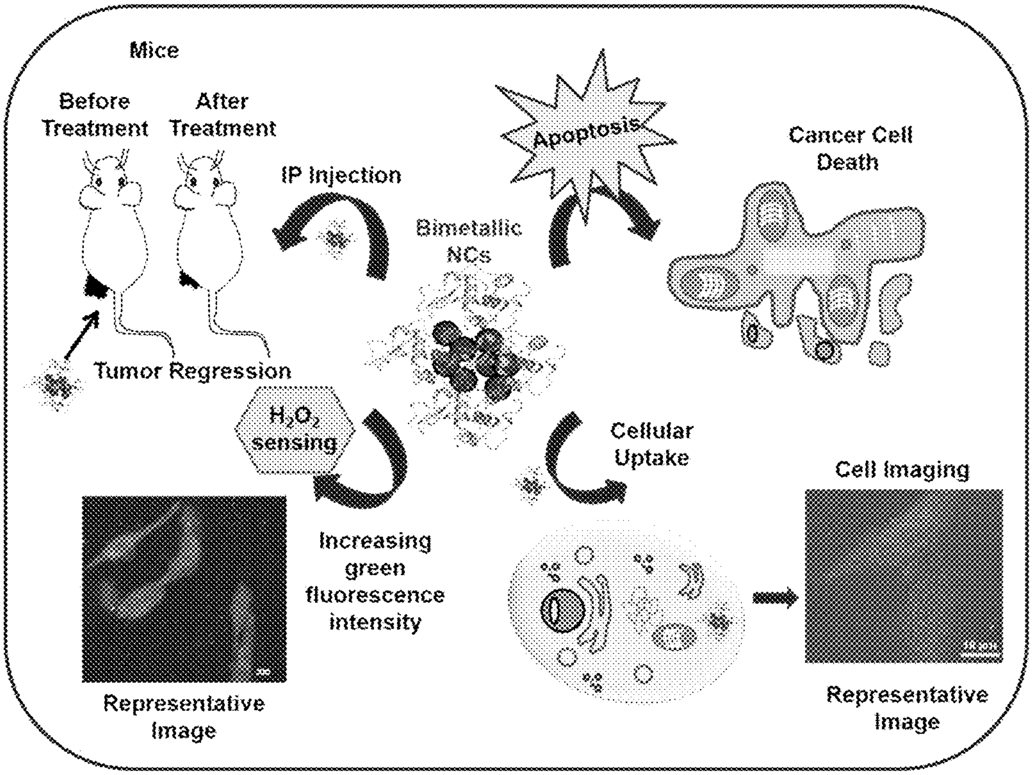
FIG. 19 represents overall scheme of cellular uptake, cell imaging, hydrogen peroxide sensing, in vivo melanoma tumor regression through i.p (intraperitonial) injection.

An overall schematic diagram is presented in FIG. 19. This schematic diagram describes the overall work as follows: (i) the formation of bimetallic NCs, (ii) cancer cell killing through apoptosis pathway, (iii) cell imaging using confocal microscopy, (iv) $H_2O_2$ sensing ability of NCs in cancer cell using confocal microscopy, (v) melanoma tumor regression in mice model.

The bimetallic nanocomposites are characterized by various physico-chemical techniques that supported their stability. The silver layer is generated from the reduction of silver nitrate. The size of the nanocomposites ranges from 100-300 nm as observed by FESEM analysis. The nanocomposites show good stability, one of the preferred criteria for biological applications. The nanocomposites display green fluorescence useful for cell imaging.

The nanocomposites exhibit cancer cells killing properties in comparison with normal cells that attribute their anti-cancer activity. The nanocomposites display hydrogen peroxide ($H_2O_2$) sensing properties (both in vitro and cell culture) as well as suppression of melanoma tumor in vivo subcutaneous model in C57/BL6 mice.

EXAMPLES

The following examples are given by way of illustration and therefore should not be constructed to limit the scope of the present disclosure.

Example 1

Example 1A: Preparation of the Ag@Au and Ag@Pt Nanocomposites (NCs)

To prepare the Ag@Au and Ag@Pt NCs, AuNPs (gold nanoparticles) and PtNPs (platinum nanoparticles) were primarily synthesized in the first step. Briefly, to prepare 150 mL of AuNPs, 50 mL of $NaBH_4$ (0.1 mg/mL) was added very slowly to a mixture of 99 mL of water and 1 mL of $10^{-2}$ M of $HAuCl_4$ solution with continuous stirring for 12 hours.

Similarly, in order to prepare 150 mL of PtNPs, 600 μL of PEG-6000 (1% w/v) was added in the mixture of 99 mL of water and 1 mL of $10^{-2}$ M of $H_2PtCl_6$ solution under stirring conditions for 30 minutes. 50 mL of $NaBH_4$ (0.1 mg/mL) in water was further added slowly into the reaction mixture under stirring conditions for the formation of PtNPs. The reactions were allowed to stir for 24 hours. The formations of the nanoparticles were observed by the changes in the colour of both the reaction mixtures. For AuNPs and PtNPs, the colour changed to ruby red and blackish grey; respectively.

Example 1B: Preparation of the Ag@Au Nanocomposites

To synthesize the Ag@Au-NCs, in the following step, $AgNO_3$ (silver nitrate) solution (334 μL: $10^{-2}$ M) was mixed with 50 mL of AuNPs solutions in molar ratio of $HAuCl_4$:$AgNO_3$=1:1 with vigorous stirring. Thereafter, 5 mL lysozyme (10 mg/mL) was then added dropwise into each of the reaction mixtures. The pH of both the reaction mixtures was adjusted to ~11 by adding NaOH (1 M). The reaction mixtures were stirred for 10 minutes at 30° C. followed by rapid addition of freshly prepared $NaBH_4$ (14.667 mL of 0.34 mg/mL stock) under stirring condition. Further, the reactions were allowed to stir for ~6 h for the formation of the NCs (Ag@Au-NCs). Finally, the NCs solutions were centrifuged at 10,000 rpm, at 20° C. for 30 minutes in Thermo scientific, Sorvall-WX ultra 100 to collect the pellets. The pellets were washed with autoclaved water thoroughly three times and finally stored at 4° C.

Example 1C: Preparation of Ag@Pt Nanocomposites

To synthesize the Ag@Pt-NCs, in the following step, $AgNO_3$ (silver nitrate) solution (334 μL: $10^{-2}$ M) was mixed with 50 mL of PtNPs solutions in molar ratio of $H_2PtCl_6$: $AgNO_3$=1:1 with vigorous stirring. Thereafter, 5 mL lysozyme (10 mg/mL) was then added dropwise into each of the reaction mixtures. The pH of both the reaction mixtures was adjusted to ~11 by adding NaOH (1 M). The reaction mixtures were stirred for 10 minutes at 30° C. followed by rapid addition of freshly prepared $NaBH_4$ (14.667 mL of 0.34 mg/mL stock) under stirring condition. Further, the reactions were allowed to stir for ~6 h for the formation of the NCs (Ag@Pt-NCs). Finally, the NCs solutions were centrifuged at 10,000 rpm, at 20° C. for 30 minutes in Thermo scientific, Sorvall-WX ultra 100 to collect the pellets. The pellets were washed with autoclaved water thoroughly three times and finally stored at 4° C.

Example 2

Figure 1A:
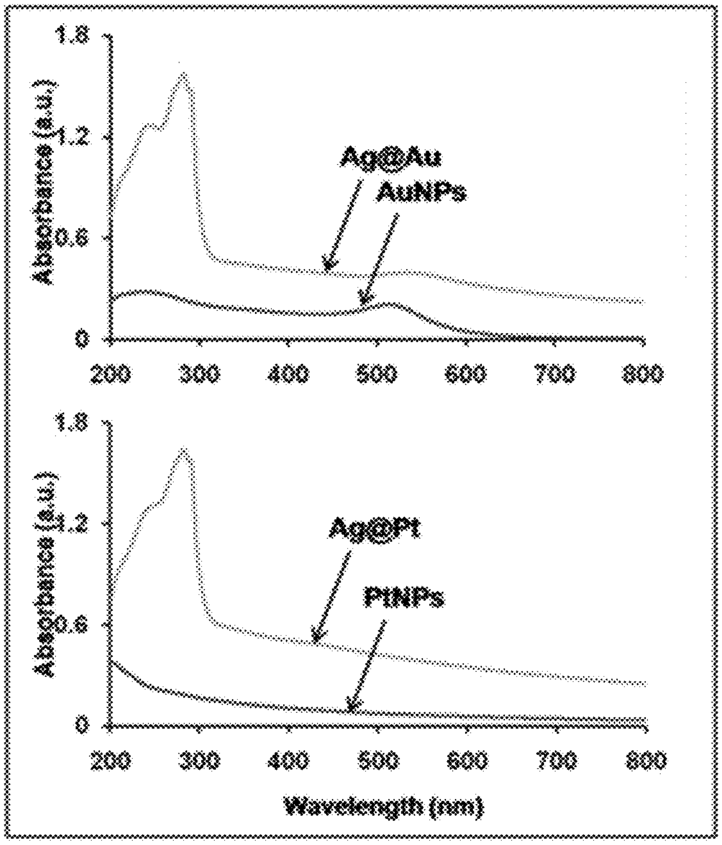
FIGS. 1A-1J represent (FIG. 1A) UV-visible spectra of synthesized [AuNPs, Ag@Au], [PtNPs, Ag@Pt]

Absorbance measurement: The formations of individual nanoparticles (AuNPs, PtNPs) as well as the NCs (Ag@Au and Ag@Pt) are observed under UV-visible spectroscopy using a quartz cuvette from range 800-200 nm using a JABCO dual-beam spectrometer (Model V-570) with 1 nm resolution. An intense absorption peak is observed at $\lambda_{max}$~515 nm, which generally attribute to the surface plasmon excitation of small spherical gold particles (AuNPs). In contrast, PtNPs exhibit an extremely weak and broad absorbance band throughout the UV-visible region. Moreover, for both Ag@Au-NC and Ag@Pt-NC all individual peaks are diminished except the peaks of lysozyme, symbolize the formation of the nanocomposites (FIG. 1A)

Example 3

Figure 1B:
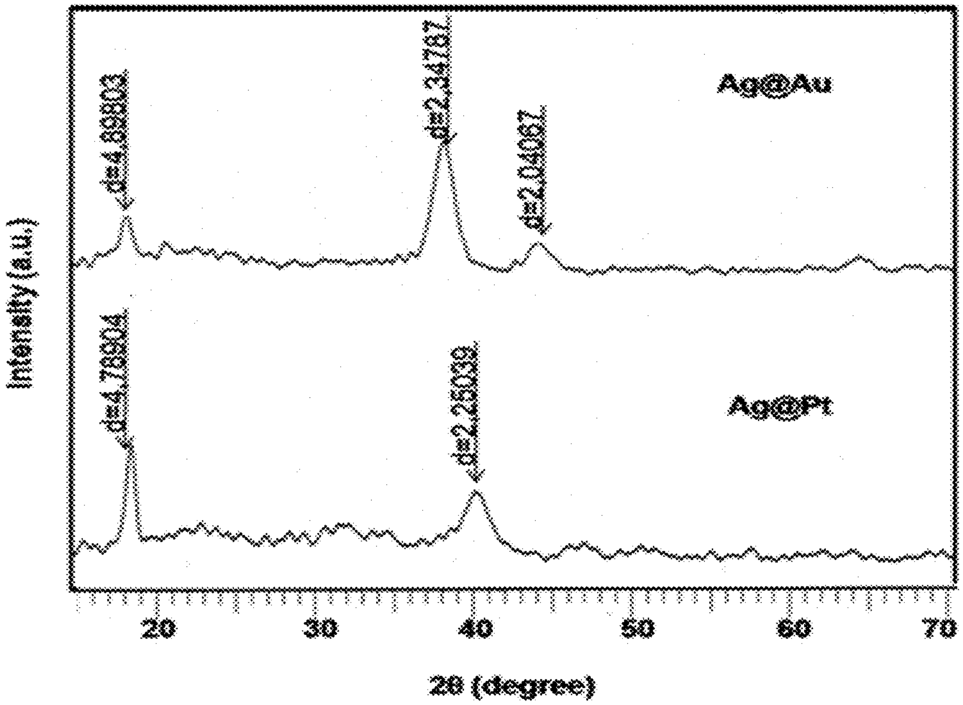

Phase purity and crystallinity measurement: The phase purity and crystallinity of nanocomposites (Ag@Au and Ag@Pt NCs) were analyzed by X-ray diffraction (XRD) analysis [Bruker AXS D8 Advance Powder X-ray diffractometer (using CuKαλ=1.5406 A radiation) in range 2θ=20 to 80°]. The pellets of the NCs were drop casted on the glass plate and submitted for XRD. The phase purity and crystal structure were determined by the XRD analysis of Ag@Au and Ag@Pt NCs. The XRD spectra of Ag@Au, Ag@Pt NCs show two distinct diffraction peaks at d=2.34787, d=2.25039 and one distinct diffraction peak at d=2.25039 respectively. No other distinctive peaks are observed within 20-80 θ (degree). This reflects less ordered poor crystalline nature of both the NCs which support the formation of bimetallic NCs (FIG. 1B).

Example 4

Figure 1C:
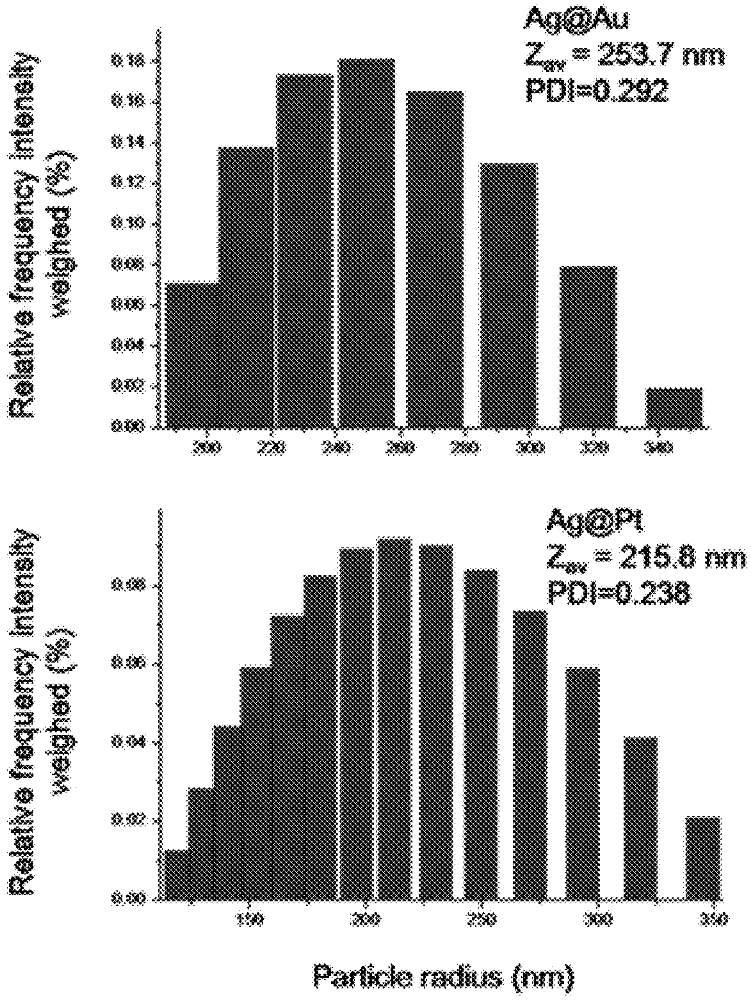

Size and surface charge measurement: The hydrodynamic radii and surface charge of as-synthesized Ag@Au and Ag@Pt NCs were monitored by dynamic light scattering (DLS) using Anton Paar, 2000. In order to check the hydrodynamic radii, 50 μL of as-prepared nanocomposites were diluted in 1 mL of mili-Q water and used in DLS measurement. Results reveal that the hydrodynamic radius of Ag@Au and Ag@Pt NCs are 253.7 nm (PDI-0.292) and 215.8 nm (PDI-0.238), respectively (FIG. 1C). Meanwhile, the zeta potential (ξ) of Ag@Au and Ag@Pt NCs are −29.2 and −59.2 eV; respectively.

Figure 1D:
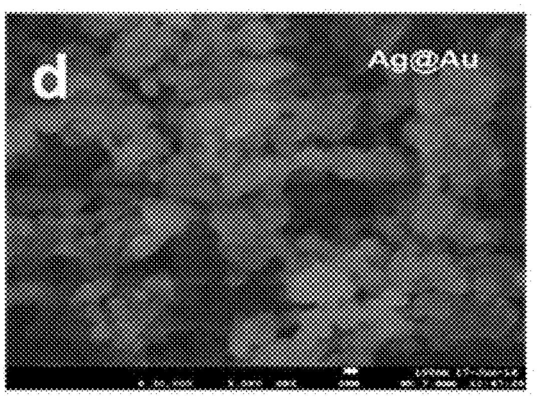
Figure 1E:
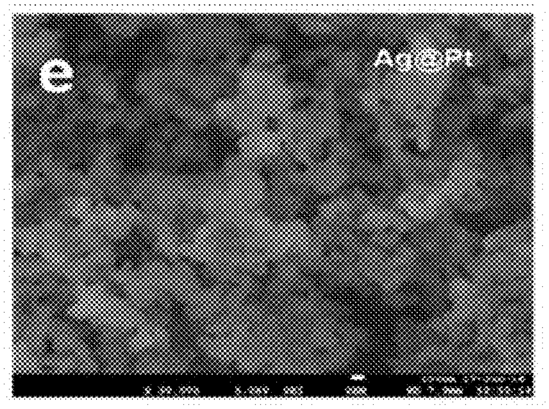
Figure 1F:
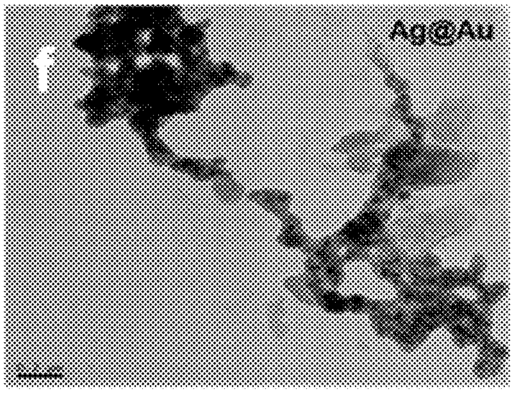
Figure 1G:
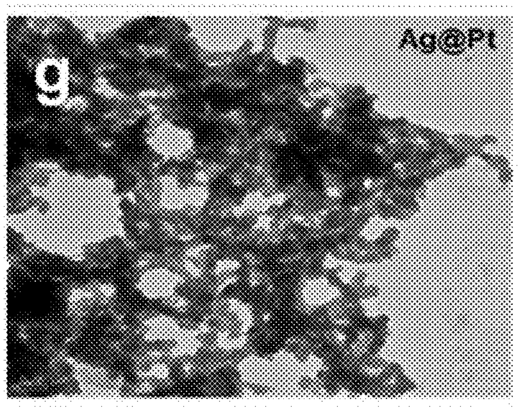
Figure 1H:
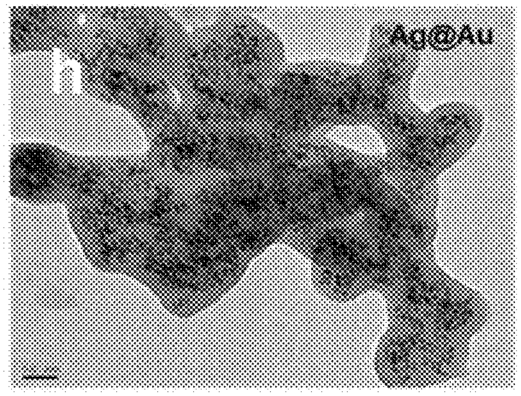
Figure 1I:
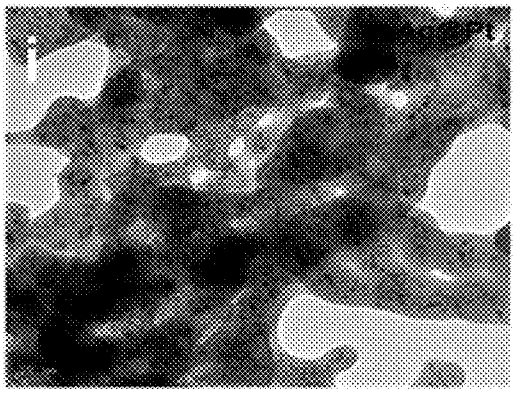

The morphology, shape of the Ag@Au and Ag@Pt NCs were further examined using the FESEM, (JEOL, 7610F). The samples were mounted in both the positions (horizontal, lateral) to observe the surface topography along with the fractured cross sections in order to examine the homogeneity. The FE-SEM images of the NCs show spherical particles with 100-300 nm in diameters which are interconnected to form the NCs (FIGS. 1D and 1E).

The actual size, shape and morphology of the as-synthesized nanocomposites were observed using the TEM (TEM: Tecnai G2 F30 S-Twin Microscope operated at 100 kV). The diluted pellets of the NCs were drop casted on the carbon-coated copper grid and allowed to dry in room temperature. The process was repeated for two more times for proper coating on the grid and analysis was performed. TEM results show that the sizes of AuNPs and as well as PtNPs within NCs are in the range of 5-10 nm and spherical in shape. These nice and spherical gold and platinum nanoparticles are dispersed within NCs. However, the outer frameworks of these NCs are formed by silver and lysozyme confirmed by the layer like framework. (FIGS. 1F, 1G, 1H, and 1I).

Example 5

Figure 1J:
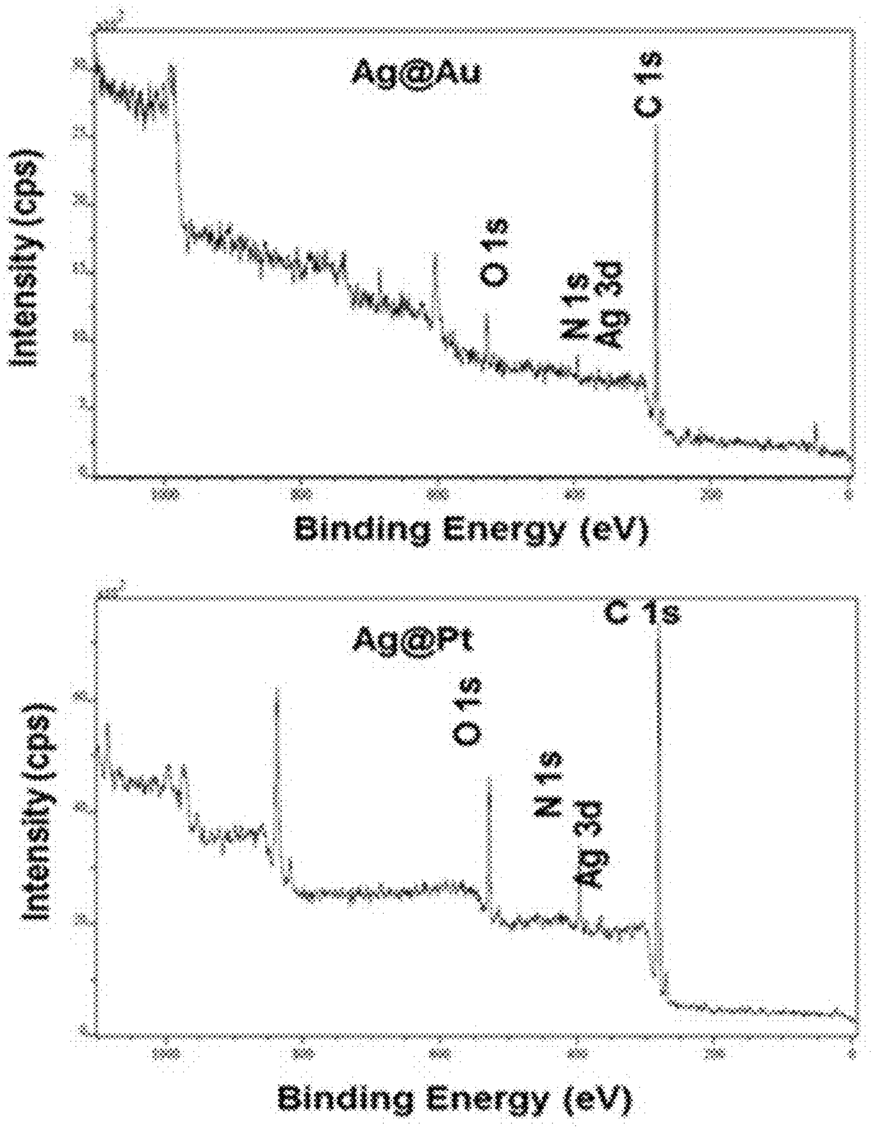

Binding energy and elemental composition measurement of Ag@Cu and Ag@Pt NCs: In order to know the elemental composition in the nanocomposites we have performed the XPS analysis [KRATOS AXIS 165 with a dual anode (Mg and Al) apparatus using the Mg Kα anode]. The pellets were drop casted on the glass plate dried and submitted for the XPS analysis. Result reveal that thepeaks at around 533, 400, 285 eV indicate the binding energies of O (1s), N (1s), C (1s); respectively of NCs. This indicates the presence of lysozyme in the NCs. The binding energy peaks appear at around 368.9 and 374.8 eV correspond to $Ag3d_{5/2}$ and $Ag3d_{3/2}$ verifies the presence of elemental silver. However, no detectable Au and Pt peaks (75-95 eV) are observed in the corresponding NCs, which clearly indicate closed silver framework with no residual uncovered AuNPs and PtNPs on the surface of NCs (FIG. 1J).

Example 6

Figure 2:
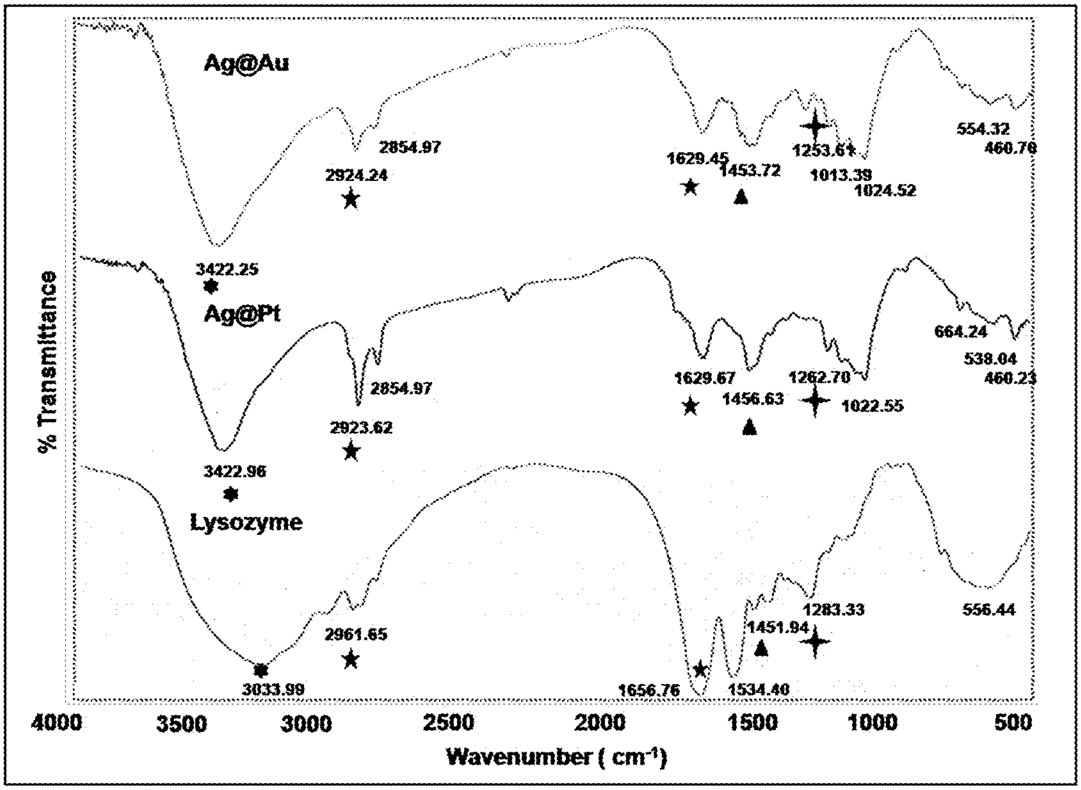
FIG. 2 represents FT-IR spectra of protein lysozyme and synthesized Ag@Au and Ag@Pt NCs.

Functional group determination: Fourier transformed infrared spectroscopy (FTIR: Thermo Nicolet Nexus 670 spectrometer) was used to determine the functional groups present in the Ag@Au and Ag@Pt NCs as well as in protein lysozyme. The FT-IR spectra were carried out at a resolution of 4 $cm^{-1}$ in KBr pellet from range 400-4000 $cm^{-1}$. The pellets obtained after centrifugation was lypholized and submitted for analysis. Results reveal that, amides I, II and III appear at 1600-1700, 1480-1575, and 1230-1300 $cm^{-1}$, respectively are present in the spectra for Ag@Au and Ag@Pt NCs due to the binding of the protein lysozyme. The —OH and —NH stretching vibrations at 3000-2900 $cm^{-1}$ are clearly distinguishable in the spectra for lysozyme. The hypsochromic shift of the —OH stretching vibration for both the NCs (3422.96 $cm^{-1}$ and 3422.25 $cm^{-1}$ for Ag@Au and Ag@Pt, respectively) compared to lysozyme (~3033.99 $cm^{-1}$) strongly support that the surface of Ag@Au and Ag@Pt are attached with the —OH bond in order to form NCs. In addition, functional groups like —$NH_2$, —COOH (overlapped with the amide II band), —SH groups help in the binding of proteins with the NCs (FIG. 2).

Example 7

Figure 3A:
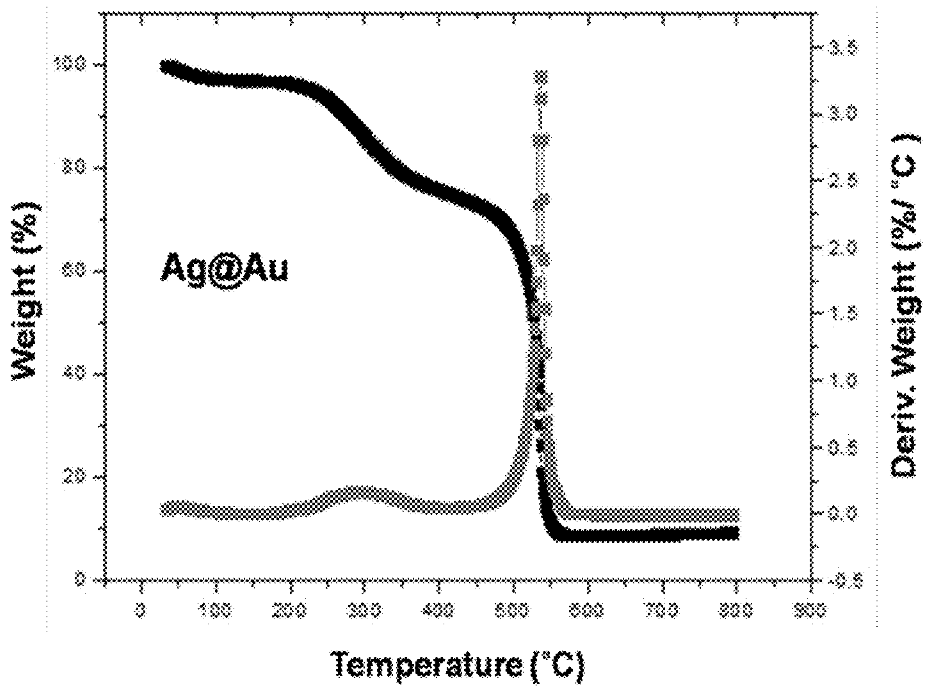
FIGS. 3A and 3B represent TGA and DTG analysis of Ag@Au (FIG. 3A) and Ag@Pt NCs (FIG. 3B).
Figure 3B:
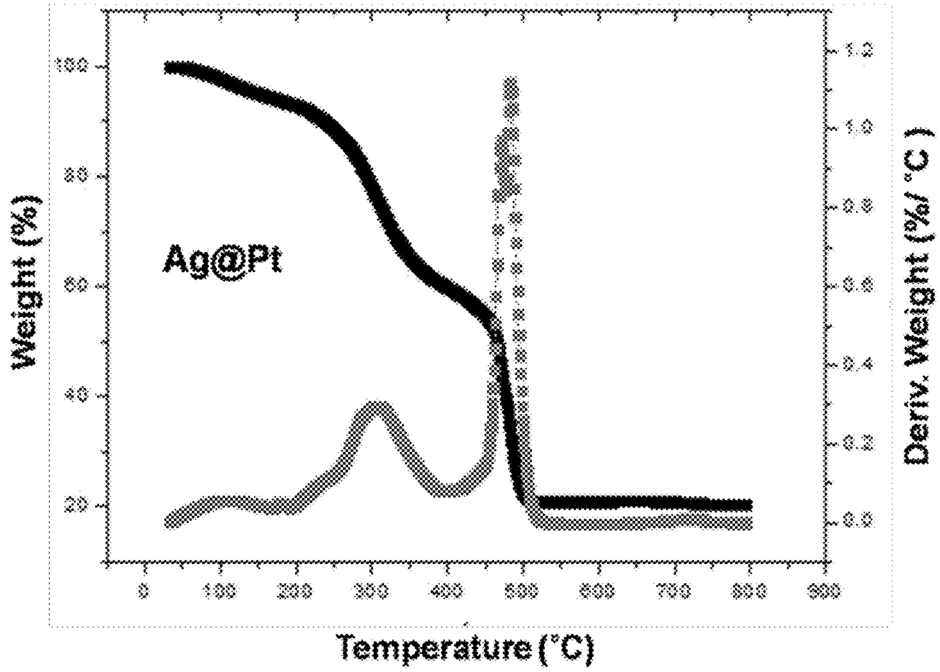

Thermal stability measurement: The thermal stability as well as the derivative (DTG) analysis of both the nanocomposites (Ag@Au NC and Ag@Pt NC) was measured using the TGA (thermo gravimetric analysis) instruments, TGA Q50 under air atmosphere from 25-800° C. The TGA profiles were measured at air atmosphere for both the nanocomposites (Ag@Au NC and Ag@Pt NC) (FIGS. 3A and 3B). The samples were heated at a rate of 10° C./min. The TGA curves demonstrated sequential two steps degradation of both the nanocomposites. Observable weight losses of the nanocomposites were found at 200-300° C. which supported the loss of water and organic molecule. This might be due to the presence of lysozyme protein as it contains the organic amino acid residues.

Example 8

ICP-OES (Inductively coupled plasma-optical emission spectroscopy) analysis of Ag@Au and Ag@Pt NCs: In order to investigate the amount of Au, Ag and Pt in NCs, ICP-OES analysis [IRIS intrepid II XDL, ThermoJarrel Ash] was carried out. The amount of Au and Pt in case of Ag@Au and Ag@Pt NCs respectively is found to be 1 μg/mL for both cases. The concentration of Ag are 6 μg/mL and 5.5 μg/mL for Ag@Au and Ag@Pt NCs; respectively. The doses of nanocomposites (NCs) used for cell culture experiments are as follows: Ag@Au NC (10 μL corresponds to 0.56 μM with respect to Ag); Ag@Pt NC (10 μL corresponds to 0.51 μM with respect to Ag).

Example 9

Figure 4:
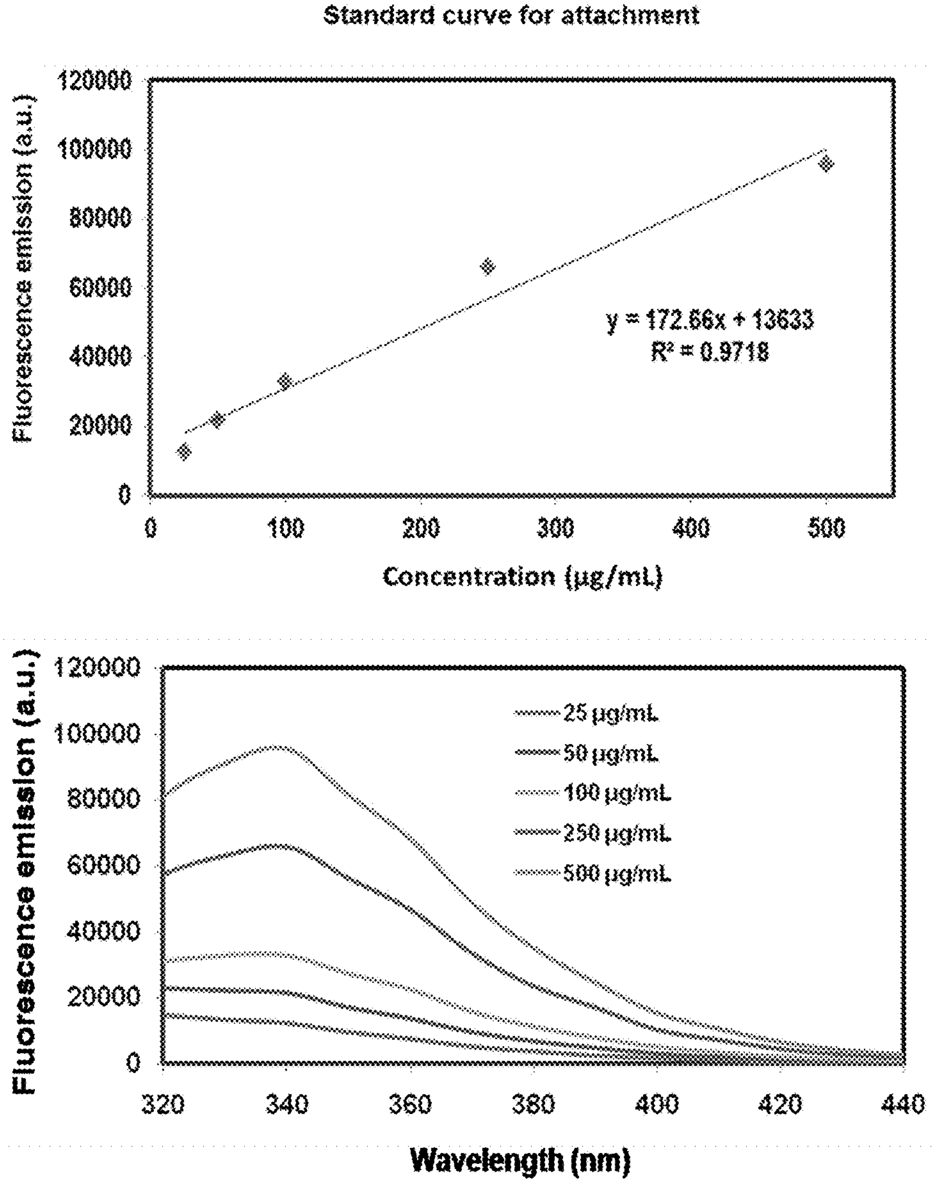
FIG. 4 represents standard curve of attachment of lysozyme with as-synthesized Ag@Au and Ag@Pt NCs and the corresponding fluorescence emission with increasing lysozyme concentrations are represented in the images.

Attachment of the lysozyme with the nanocomposites: We have calculated the % of attachment of lysozyme obtained from the standard curve using fluorescence spectroscopy considering the fluorescence emission intensity of lysozyme at $\lambda_{em}$~340 nm (excitation at 280 nm). We found that ~30% of the lysozyme is attached for both the NCs (FIG. 4).

Example 10

Figure 5A:
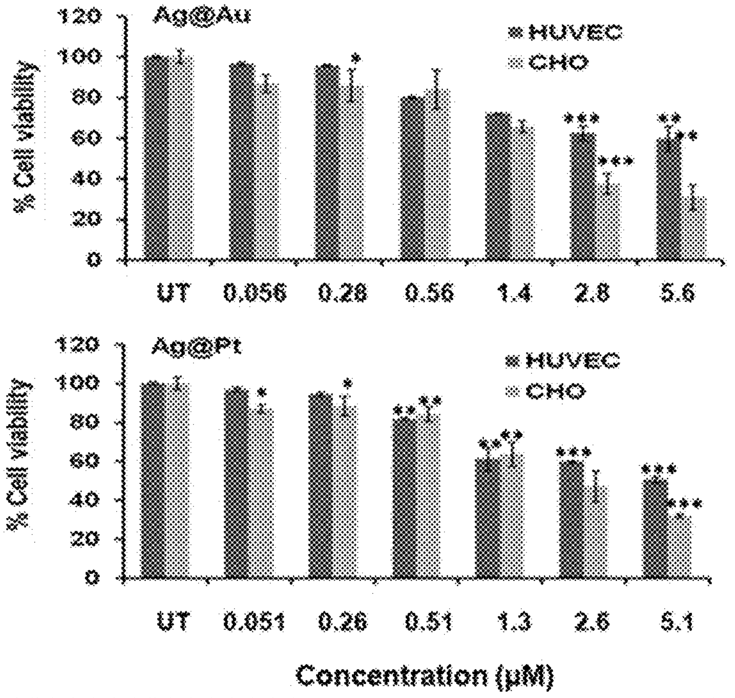
FIGS. 5A and 5B represent dose-dependent in vitro cytotoxicity of Ag@Au and Ag@Pt NCs. In vitro cell viability (MTT) assay in (FIG. 5A) HUVEC, CHO (FIG. 5B) B16F10, MCF7, MDA-MB-231 cells incubated with Ag@Au and Ag@Pt in dose dependent manner 0.056-5.56 μM w.r.t Ag; Ag@Pt: 0.051-5.1 μM w.r.t Ag, as measured using ICP-OES analysis for 24 h, TTEST, *P" 0.05, P" 0.005, *P" 0.0005 compared to UT.
Figure 5B:
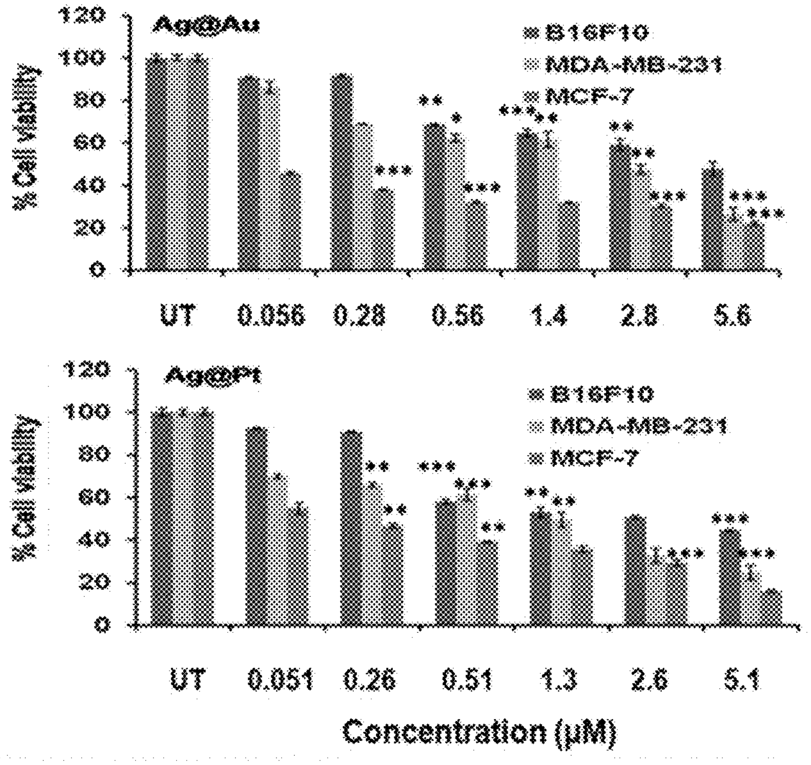

Cell viability assay: Briefly, cancer cells (B16F10, MDA-MB-231, MCF-7) and normal cell (CHO; EA.hy926) were seeded in 96 well tissue culture plate ($10\times10^3$ cells/well) and grown in DMEM for 24 h in the presence of 5% $CO_2$ at 37° C. HUVECs were also seeded in 96 well tissue culture plates at the same density and grown to confluence in EBM media. Further, of Ag@Au and Ag@Pt NCs were added in a dose dependent manner to the cells and kept for 24 h in similar conditions. The surface attached nanomaterials in the treated cells were extensively washed with DPBS. Further, the cell viability assay using MTT reagents was performed according to our published procedure. Results revealthat there is a dose dependent decrease in the cell viability in cancer cells as compared to normal cells (FIGS. 5A and 5B). Monitoring the cell viability in different cell lines, we can conclude that both the compounds have low toxicity in normal cells compared to cancer cells and therefore can be useful as therapeutic agent for cancer treatment in near future.

Example 11

Figure 5C:
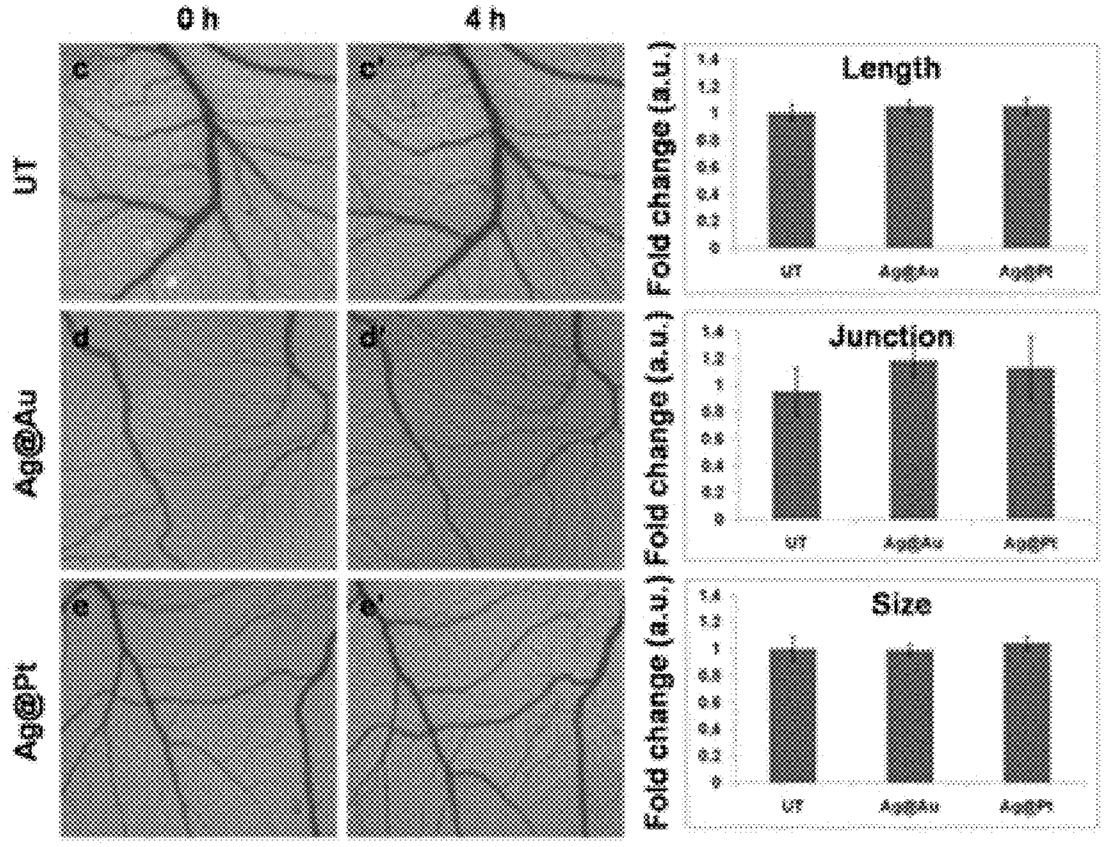
FIG. 5C presents (c-e) CAM assay with nanocomposites for in vivo angiogenesis: chick embryo incubated with (c, c'), nothing (UT), (d, d') Ag@Au, (e, e') Ag@Pt, respectively showing biocompatible nature of the nanocomposites. The fold changes with respect to length, junction and size were measured using the Angioquant software.

CAM assay (chick chorioallantoic membrane): The chorioallantoic membranes from the chick are widely used in various biological applications in order to check the in vivo angiogenesis, biocompatibility etc. Here, in this study, the fertile eggs were kept in an incubator at 37° C., 60-70% humidity. On the fourth day of incubation, a small hole was created on the shell and a miniscule amount of the albumin was drained out using a micropipette. Then, the egg shell was broken and peeled off from the top to create a window in order to expose the embryo. Eventually, the treatments of NCs [Ag@Au-NC; Ag@Pt-NC] were given. The eggs were further incubated for 4 h in the incubator. The pictures were taken at 0 h and 4 h using Leica Stereo Microscope. Results indicate that there are no significant differences of the length, junction and size of blood vessel of the treated groups compared to UT as quantified using the Angioquant software (FIG. 5C)

Example 12

Figure 6:
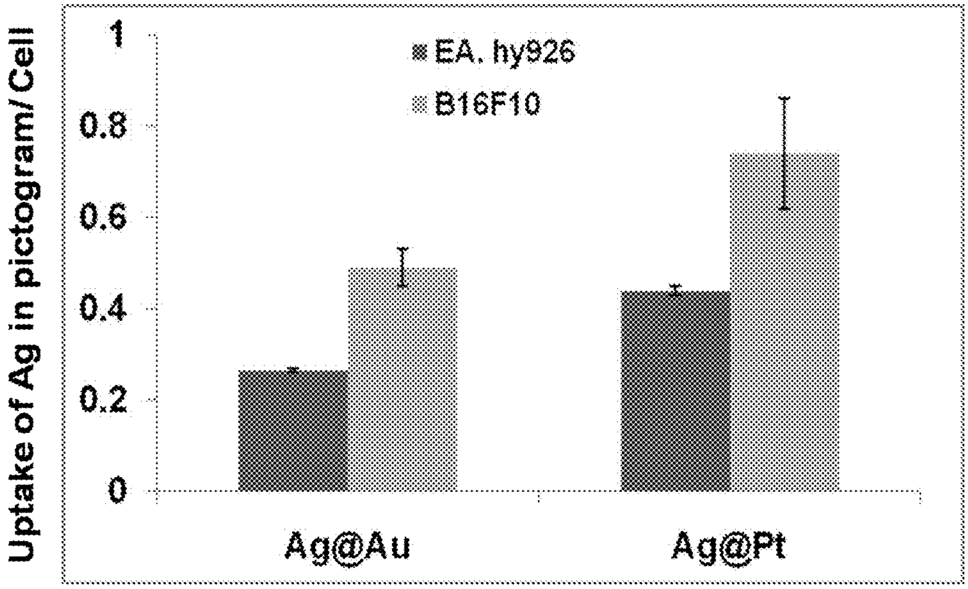
FIG. 6 represents the cellular uptake study in vitro using ICP-OES analysis in B16F10 and EA.hy926 cell line.

Uptake study by ICP-OES: Cancer cell (B16F10) as well as normal cell (EA.hy926) were plated in $T_{25}$ flask at a density of $10\times10^5$ cells/plate and grown for 24 h in cell culture conditions. After 80% confluence, cells were treated with Ag@Au and Ag@Pt NCs and incubated for 6 h. Cells were then washed with PBS to remove the unbound particles, trypsinized, and the cells were counted using the heamocytometer. The pellets were digested with concentrated nitric acids, submitted for ICP-OES. Result exhibit that the uptake of Ag per unit cell in cancer cell is much more than normal cell (FIG. 6).

Example 13

Haemolytic assay in vitro: In order to know the hemocompatibility of the Ag@Au and Ag@Pt NCs, 2 mL of mice blood was collected and 0.5 ml of heparin was added as an anticoagulant. The sample was centrifuged at 3000 rpm for 10 minutes at 4° C. and the erythrocytes were collected. They were washed thrice using PBS buffer and the supernatant was removed. The pellet was suspended in 10 mL PBS which was used as stock solution. Portions of 0.1 mL of the erythrocytes suspension were added to 0.9 mL each of PBS buffer and tap water and considered as negative and positive controls, respectively. The different concentrations of NCs were mixed with 100 μL of erythrocytes suspension; the volume was made up to 1000 μL using the HBSS buffer. The samples were incubated on the water bath shaker for 90 minutes at 37° C. The samples were centrifuged at 3000 rpm, 10 minutes at 4° C. Finally, the supernatant was used to determine the absorbance. Ultimately, the absorbance was measured at 541 nm using multimode reader.

% of hemolysis=(O.D. of NCs−O.D. of negative control)/(O.D. of positive control−O.D. of negative control)×100

Figure 7:
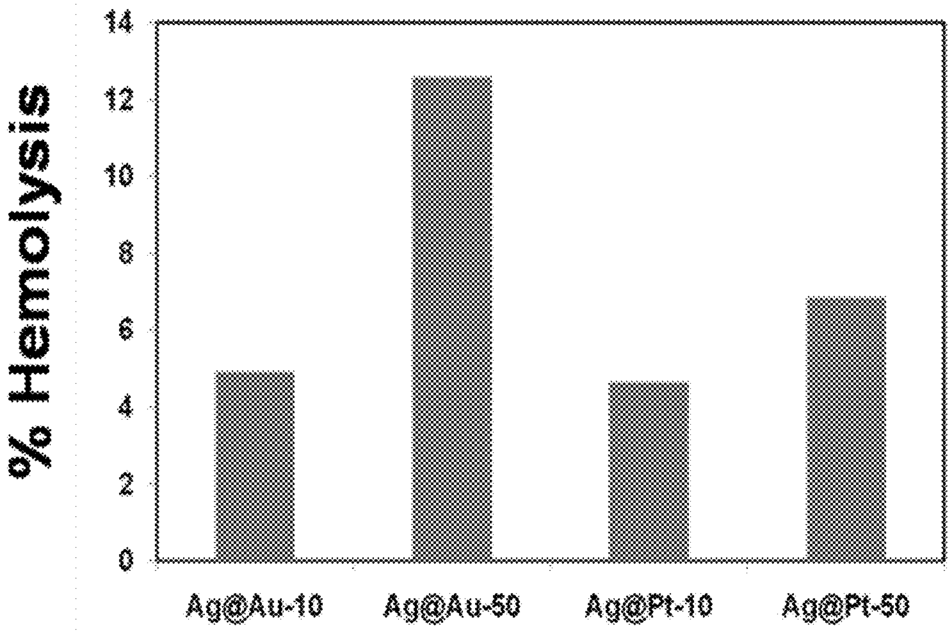
FIG. 7 represents percentage of the hemolysis in mouse blood after treatment with the Ag@Au and Ag@Pt NCs.

The results demonstrate that the doses used for cell culture experiments in case of Ag@Au and Ag@Pt NCs are highly hemocompatible (<5% hemolysis) (FIG. 7). This data also supports the potential applicability of NCs in vivo.

Example 14

Figure 8A:
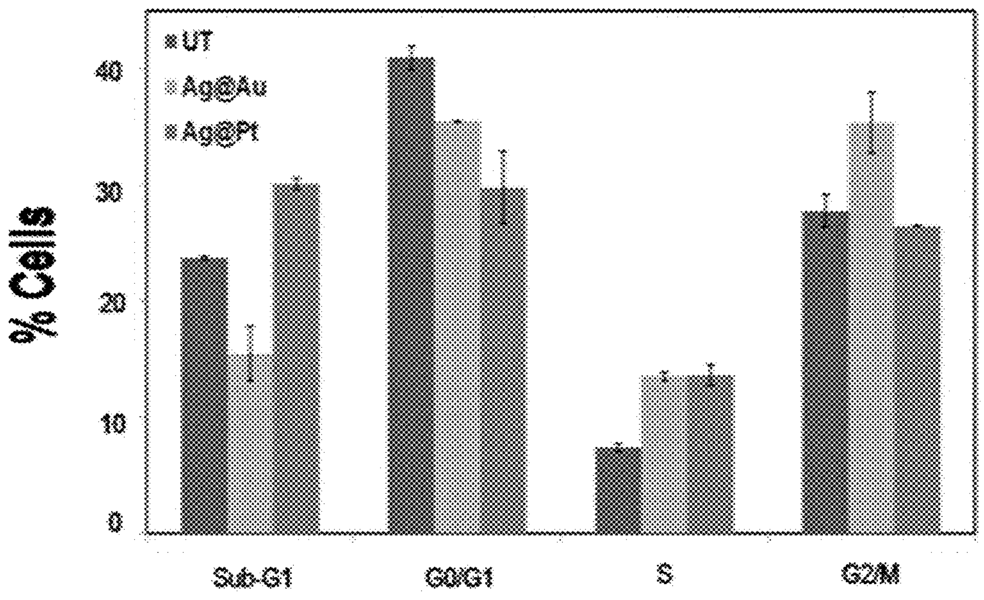
FIGS. 8A-8E represents (FIGS. 8A and 8B) Quantification of FACS (FIG. 8A) MCF 7 cells and (FIG. 8B) B16F10 cells treated with Ag@Au [10 μL of nanopellet/mL of media; 0.56 μM w.r.t Ag] and Ag@Pt [Ag@Pt (10 μL of nanopellet/mL of media; 0.51 μM w.r.t Ag] NCs show the G2/M phase and sub-G1 phase arrest in cells.
Figure 8B:
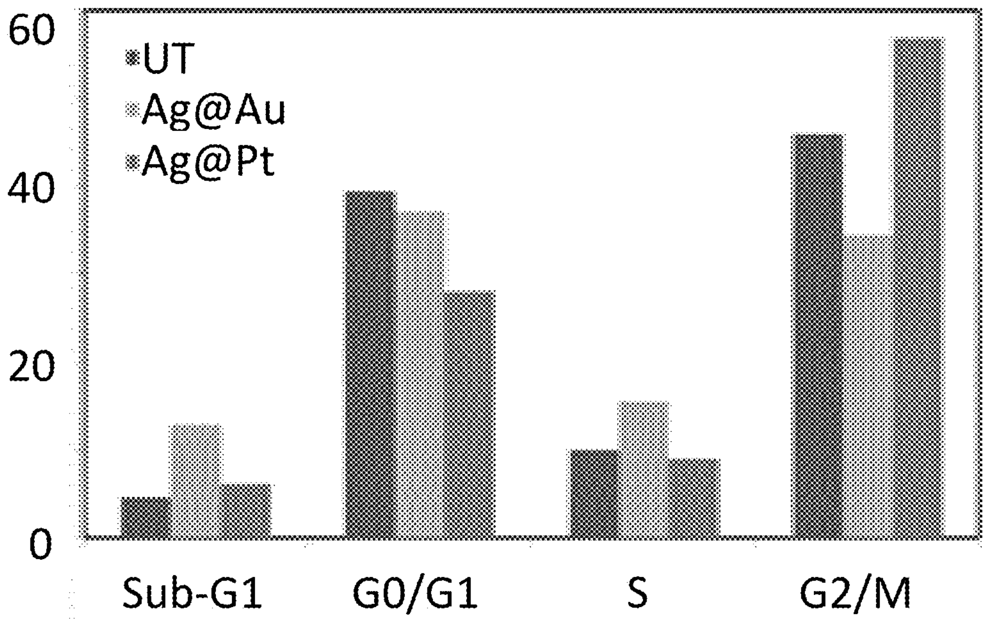

Cell cycle arrest and apoptosis studies using FACS: Cancer cells (MCF-7 and B16F10; $5\times10^5$ cells) were seeded in DMEM media in 60 mm dish. MCF-7 cell as well as B16F10 cell were incubated with Ag@Au-NC pellet for 24 h and 36 h; respectively. The trypsinized cells were fixed in 70% ethanol. Afterwards, the cells were washed, processed according to our published procedure using PI staining in a flow cytometer (FACS Canto II, Becton Dickinson, San Jose, CA, U.S.). The data were analyzed with the help of F3 express software. Results demonstrate that Ag@Au NC treated MCF7, B16F10 cells show significant amount of cell cycle arrest in mitotic phase (G2/M phase) and sub-G1 phase (FIG. 8A). In contrast, higher populations of cells are found to be arrested in the early sub-G1 phase for Ag@Pt NC treated as compared to control for MCF7 cells and in G2/M phase for B16F10 cells (FIG. 8B). Thus, cell cycle results clearly substantiate with the fact that NCs could stop the cancer cell proliferation and useful for theranostics applications.

Figure 8C:
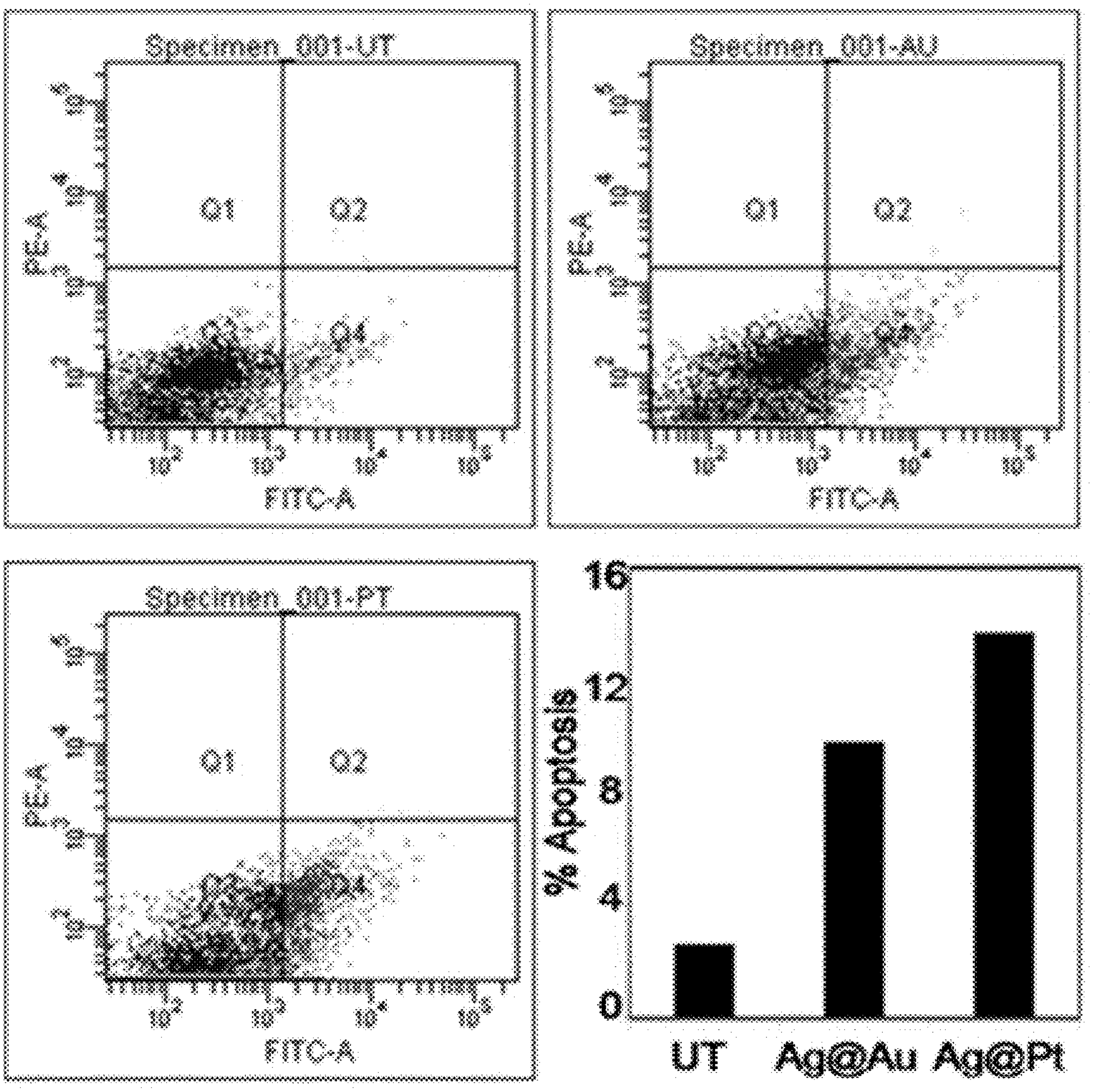
Figure 8D:
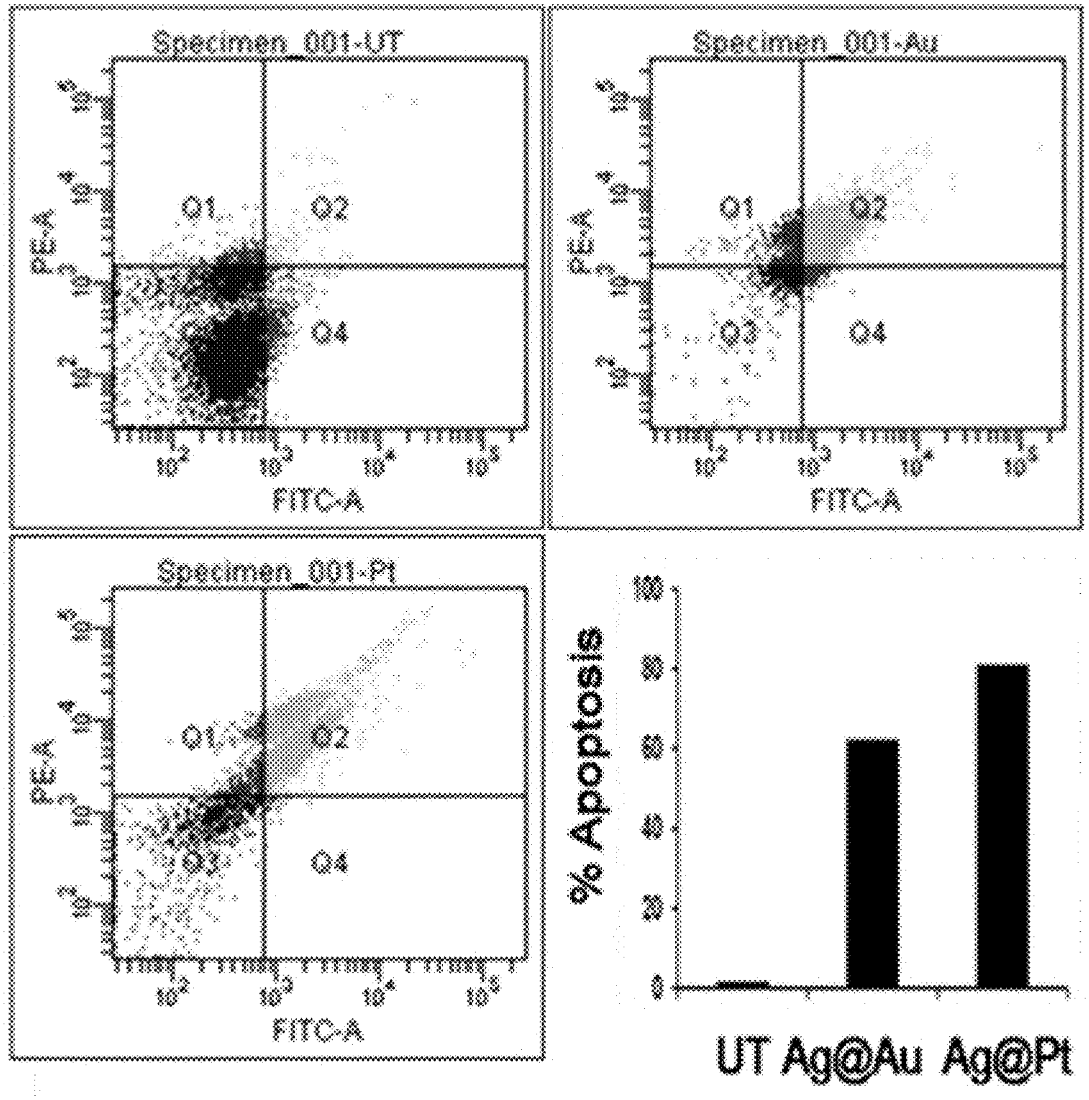

Briefly, MCF-7 and B16F10 cells; ($5\times10^5$ cells) were seeded in 60 mm dish for 18-24 h prior to treatment. After incubation with Ag@Au and Ag@Pt NCs for 24 h (MCF7), 30 h (B16F10), respectively; cells were washed with DPBS followed by trypsinization. Finally, the cells were processed through Annexin V-FITC staining as per manufacturer's instructions. Treatment with both the NCs distinctly show the accumulation of cancer cell (MCF7) in early apoptotic zone compared to control and late apoptotic zone for B16F10 cells (FIGS. 8C and 8D). The data clearly indicate the apoptosis inducing effect of NCs on cancer cells. The apoptotic cell deaths appear to contribute to the anticancer effects of NCs.

Example 15

Silver ion release study from the NCs: One of the fundamental reasons by far is the release of silver ions (Ag+) from the system that elevates the production of ROS and increases the level of ROS responsive genes which eventually responsible for DNA damage, decreases in mitochondrial activity thus leading to apoptosis.

Figure 8E:
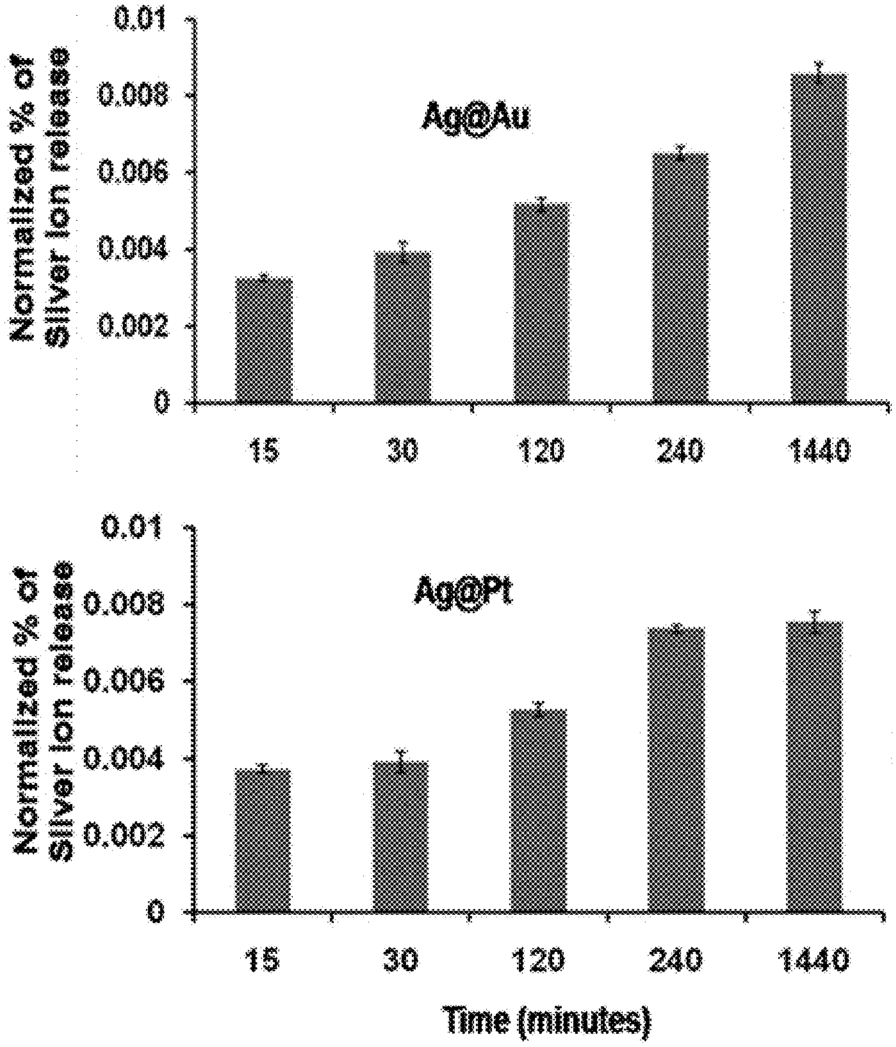

The release kinetics of silver ion from Ag@Au and Ag@Pt NCs in pH=7.4 (physiological pH) was studied using ICP-OES analysis in a time dependent manner. Results reveal that the release of silver ion from Ag@Au NC start 15 min after the incubation time and slow sustains release is observed up to 24 h. Similarly, Ag@Pt NC also exhibit maximum release of silver ion at 1440 min (24 h) (FIG. 8E). So, from the release profile of silver ions from the NCs system it can be concluded that our synthesized bimetallic Ag@Au and Ag@Pt NCs can act as an anti-cancer agent. Hence, it is to be deemed that both the NCs offer a great deal in the upcoming future on cancer theranostics.

Example 16

Evaluation of tumor regression by NCs: The tumor regression study of Ag@Au and Ag@Pt NCs were evaluated using female mice (C57BL/6J) implanted with the mouse melanoma cancer cell line, B16F10. Approximately, $2.5\times10^5$ B16F10 cells were resuspended in 100 μL of HBSS. Cells were then inoculated at a subcutaneous site (s.c) i.e. into the lower right abdomen of female mice aged 6 weeks. When tumor volume reached approximately 50-100 $mm^3$ after 10 days of injection, mice were randomly allocated into three groups (n=3) including (i) UT group (no treatment), (ii) Ag@Au NC treated (0.1 mg/kg w.r.t Ag) group, (iii) Ag@Pt NC treated (0.1 mg/kg w.r.t Ag) group. All the treatments were intra-peritoneally (IP) injected on four alternative days over a period of 10 days using a tuberculin syringe. The anti-tumor activity of Ag@Au and Ag@Pt NCs was evaluated by measuring tumor volume $[(a\times b^2)/2]$, where 'a' is the major diameter and 'b' is the minor diameter at various time points after injection. All the animals were monitored carefully for clinical signs (body weight gain or loss, morbidity and mortality) everyday throughout the whole experimental days. In order to study the survivability of the mice after administering the NCs, we kept the mice separately considering the aforesaid groups (UT, Ag@Au NC, Ag@Pt NC) so that each group contained three mice.

Figure 9A:
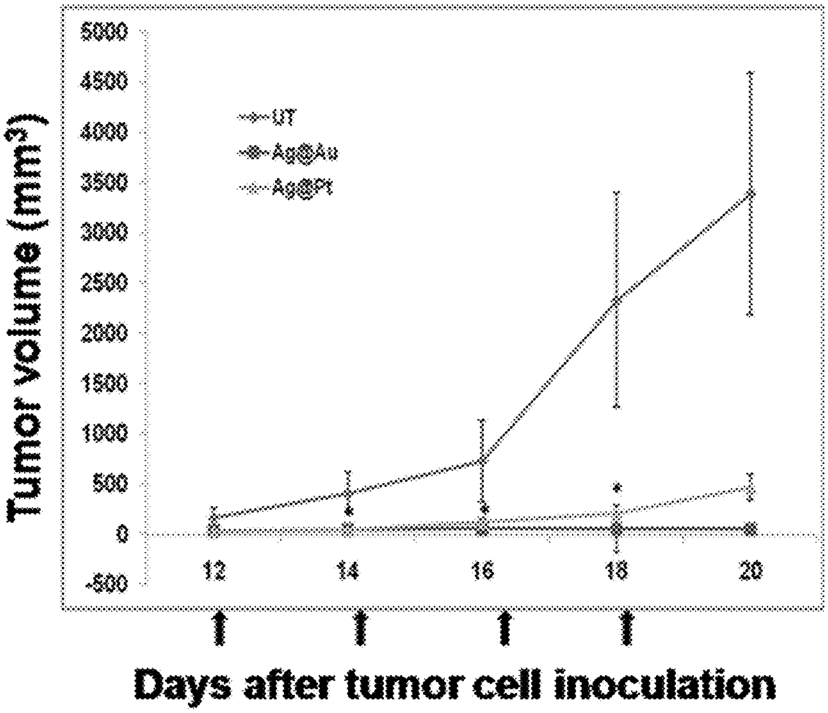
FIGS. 9A-9F represents In vivo anticancer study (FIG. 9A) Tumor regression after subcutaneous inoculation of B16F10 cell into C57BL6/J mice followed by intraperitoneal treatment either with Ag@Au, Ag@Pt, or untreated (UT)
Figure 9B:
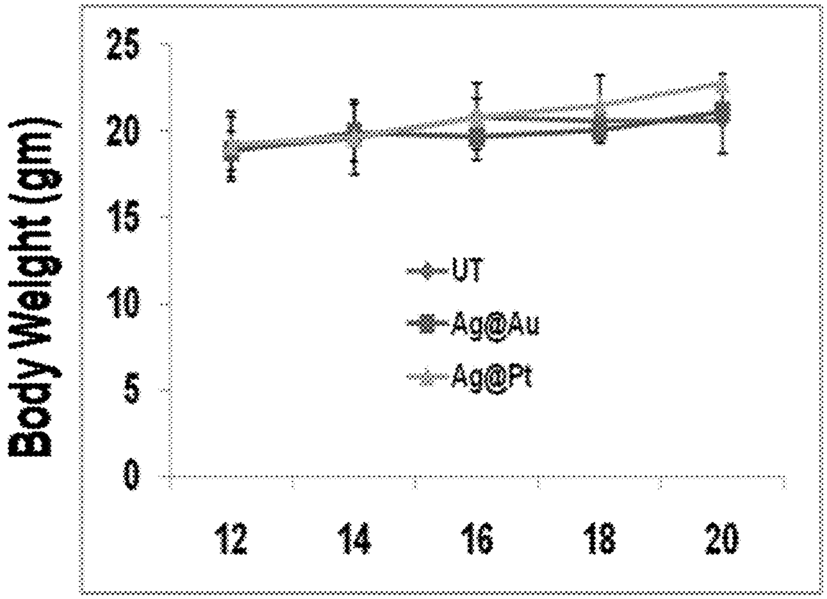
Figure 9C:
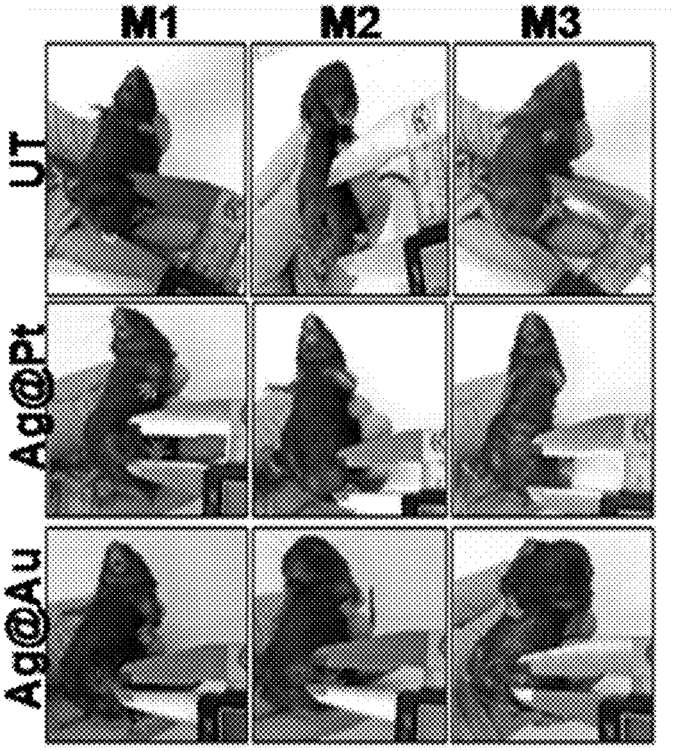
Figure 9D:
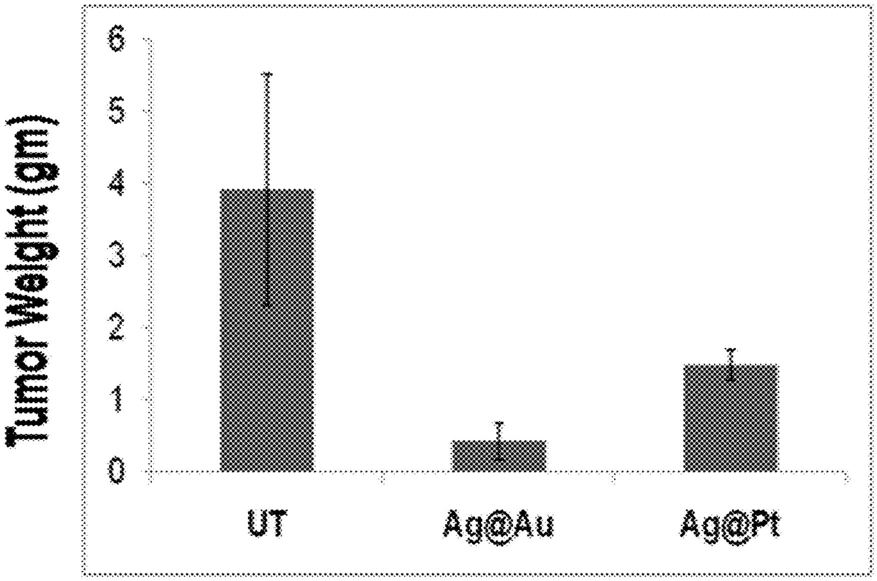
Figure 9E:
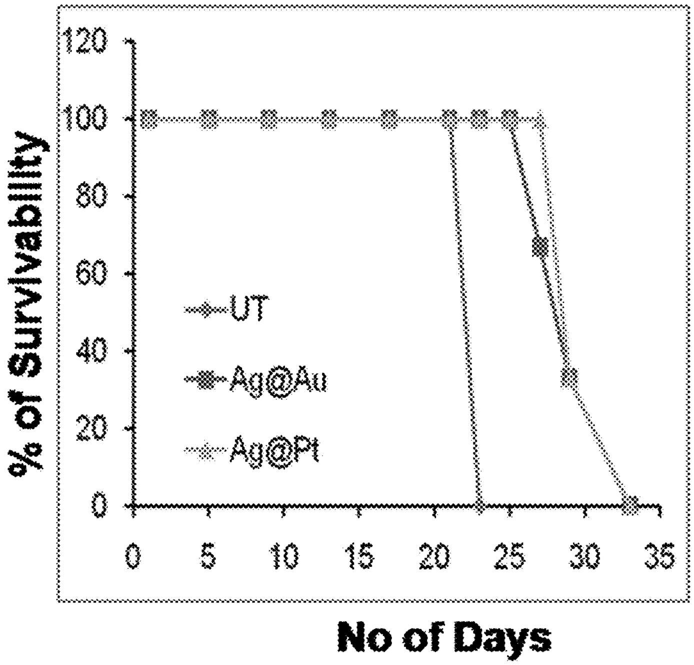

Results reveal that, Ag@AuNC exhibits superior anti-tumor activity compared to Ag@Pt NC treated group. But, both the NCs treated groups show significant tumor volume regression in a time dependent manner compared to UT group (FIG. 9A). There are no significant changes in the body weight of the between the UT and treated groups (FIG. 9B). The representative mouse images are shown in FIG. 9C. We also measured the tumors weight in sacrificed mice and found out marginally lower weight in NCs treated groups (Ag@Au and Ag@Pt) compare to UT group (FIG. 9D). The results clearly stipulate the fact that there is no adverse side effect of treated materials on normal physiological functions in animals. It is therefore recorded that mice treated with Ag@Au and Ag@PtNCs show improved survivability compared to untreated mice for almost 10 days (FIG. 9E). Optimizing all these data it is clear that these NCs open a new window in the field of cancer nanotechnology.

Example 17

Figure 9F:
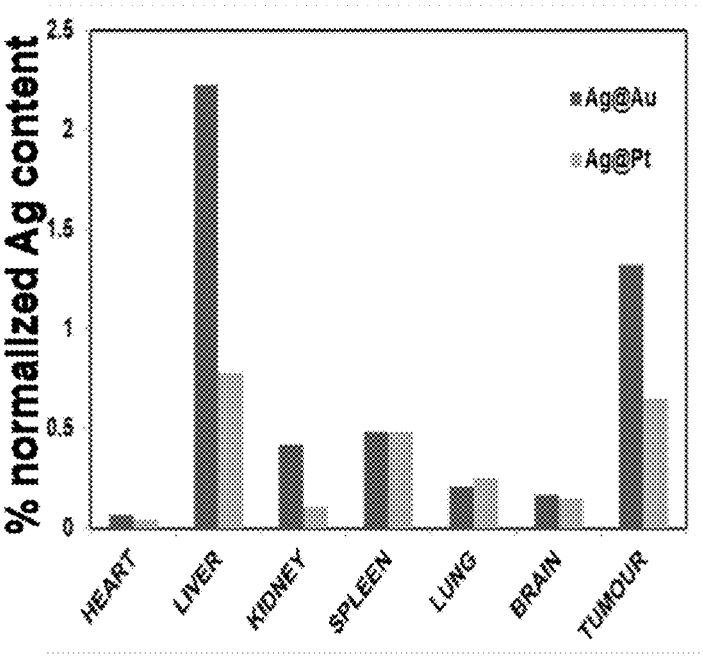

Bio-distribution of silver (Ag) in mice: We collected all the vital organs along with the tumors from the sacrificed C57BL/6J female mice bearing B16F10 tumor (aggressive) after treatment with Ag@Au NC and Ag@Pt NC. All the organs as well as tumors were collected, weighed and kept at −80° C. for overnight in DPBS. Finally, all the organs and tumor samples were digested with 70% concentrated $HNO_3$ according to their weight and submitted for ICP-OES analysis. From there we calculated the % normalized Ag content in the respective samples. Results exhibit that the distribution of Ag is higher in tumor rather than other organs except liver (FIG. 9F). This data actually reflects the tumor specific more uptake of Ag owing to EPR effect.

Example 18

Figure 10:
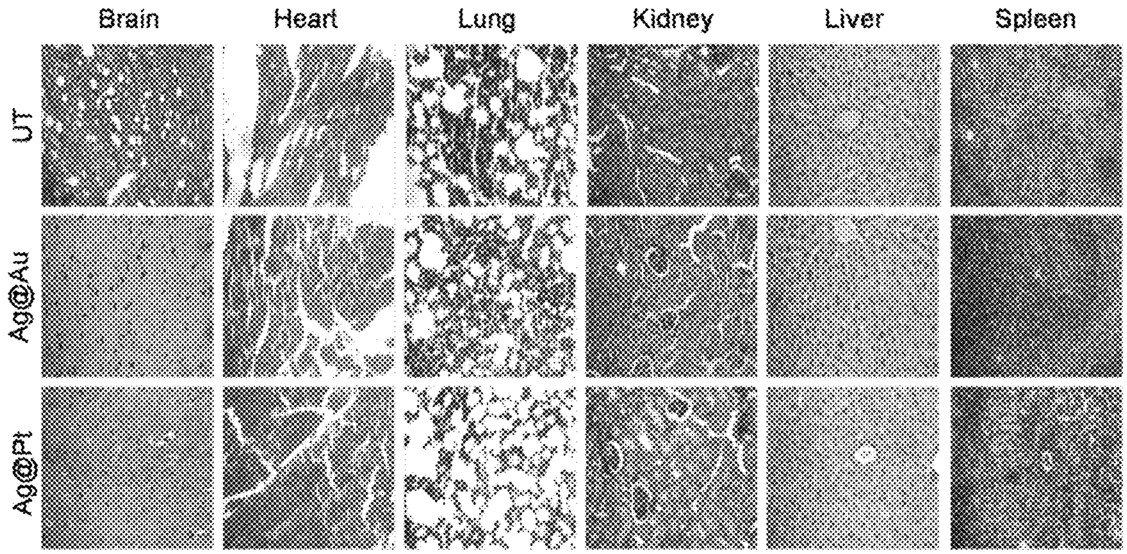
FIG. 10 represents H&E stained histopathological sections of the major organs of C57BL6/J female mice from the treated groups (Ag@Au, Ag@Pt, Dox) and UT (control) groups and mice treated.

Histopathological examination: In order to identify any abnormalities on the animal's vital organs, histopathological examination was carried out after sacrifice of mice. We collected the vital organs (brain, liver, heart, kidney, lung and spleen) of the untreated and treated mice Ag@Au NC and Ag@Pt NC. The histological appearances of the liver, spleen, kidney, brain, heart, and lung were observed after haematoxylin-eosin (H&E) stain. Further, the tissues were fixed with 10% formalin, subjected to standard tissue processing and were embedded in paraffin blocks. Thereafter, they were sectioned at a thickness of 5 μm and mounted on the glass slides. Hematoxylin-eosin (H&E) staining was performed according to the literature. Bright-field images were acquired using a microscope. The mice treated with both the NCs showed no significant toxicity to the tissue such as inflammation, vascular changes or depletion fibrosis etc (FIG. 10).

Example 19

Figure 11:
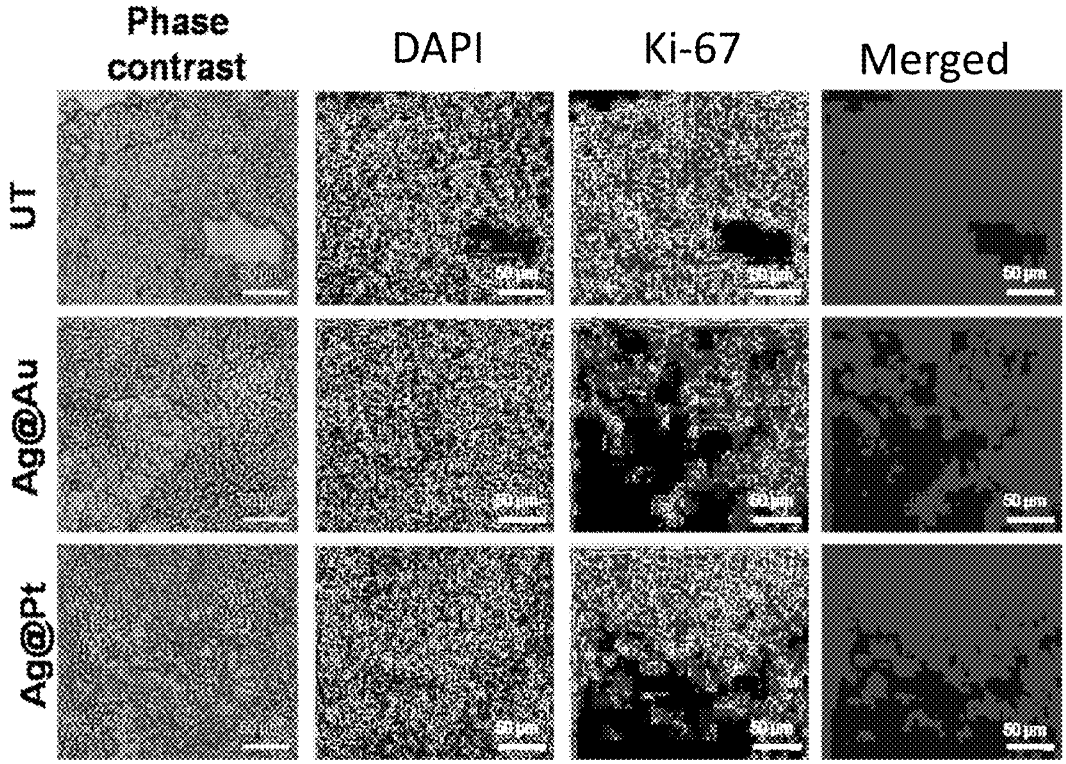
FIG. 11 represents Ki-67 expression in immunofluorescence study for proliferating cells. Microscopic pictures of tumor sections of UT group (first row), Ag@Au treated group (second row) and Ag@Pt treated group (third row). First column from left shows the tissue architecture in bright field. Second column shows the nucleus stained by DAPI, third column stained with Ki-67 marker (red fluorescent) and fourth column shows the merged images. All the pictures were taken in 20× magnification.

Immunofluoresence studies: Prior to immunostaining the tumor tissue slides were dipped into isopropanol followed by xylene for 3 minutes each and antigen retrieval was carried out by heating section in sub-boiling condition in 10 mM citrate buffer (pH=6) for 10 minutes. Tissue sections were washed locally with mili-Q water three times after cooling the slides at room temperature. After that, blocking was performed with 3% BSA solution in 1×TBST for 1 h at room temperature. Then the sections were washed for three times with 1×TBST for about five minutes each. Sections were then incubated in primary antibody (Ki-67) at 4° C. overnight. The sections were washed with 1×TBST followed by addition of secondary antibody and incubation for half an hour at room temperature. Finally, after washing the sections with 1×TBST, they were mounted with DAPI fluoroshield. The images were captured using fluorescence microscope (Nikon Eclipse: TE 2000-E, Japan) at 20× magnification. Result reveal that Ag@Au and Ag@Pt NCs treated tumor tissues show suppressed red fluorescence compared to untreated, treated tissue sections (FIG. 11). The anti-tumor activities of both the NCs are clearly proved by the decrease in expression of Ki-67 in cells.

Example 20

Figure 12:
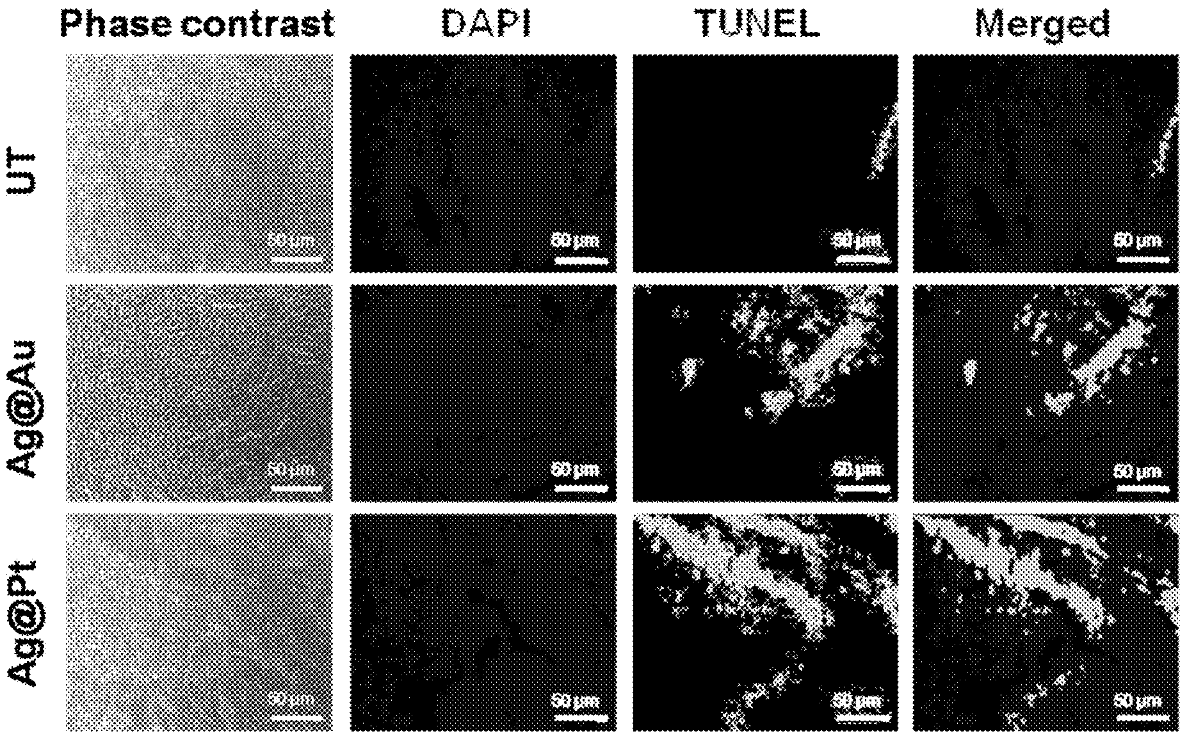
FIG. 12 represents effect of treated and untreated groups in tumor vasculature. Microscopic pictures (at 20× magnification) of tumor sections of UT group (first row), Ag@Au treated group (second row) and Ag@Pt treated group (third row). First column from left shows the tissue architecture in bright field. Second column shows the nucleus stained by DAPI, third column shows the apoptotic regions in TUNEL assay (green fluorescent) and fourth column shows the merged images.
Figure 13:
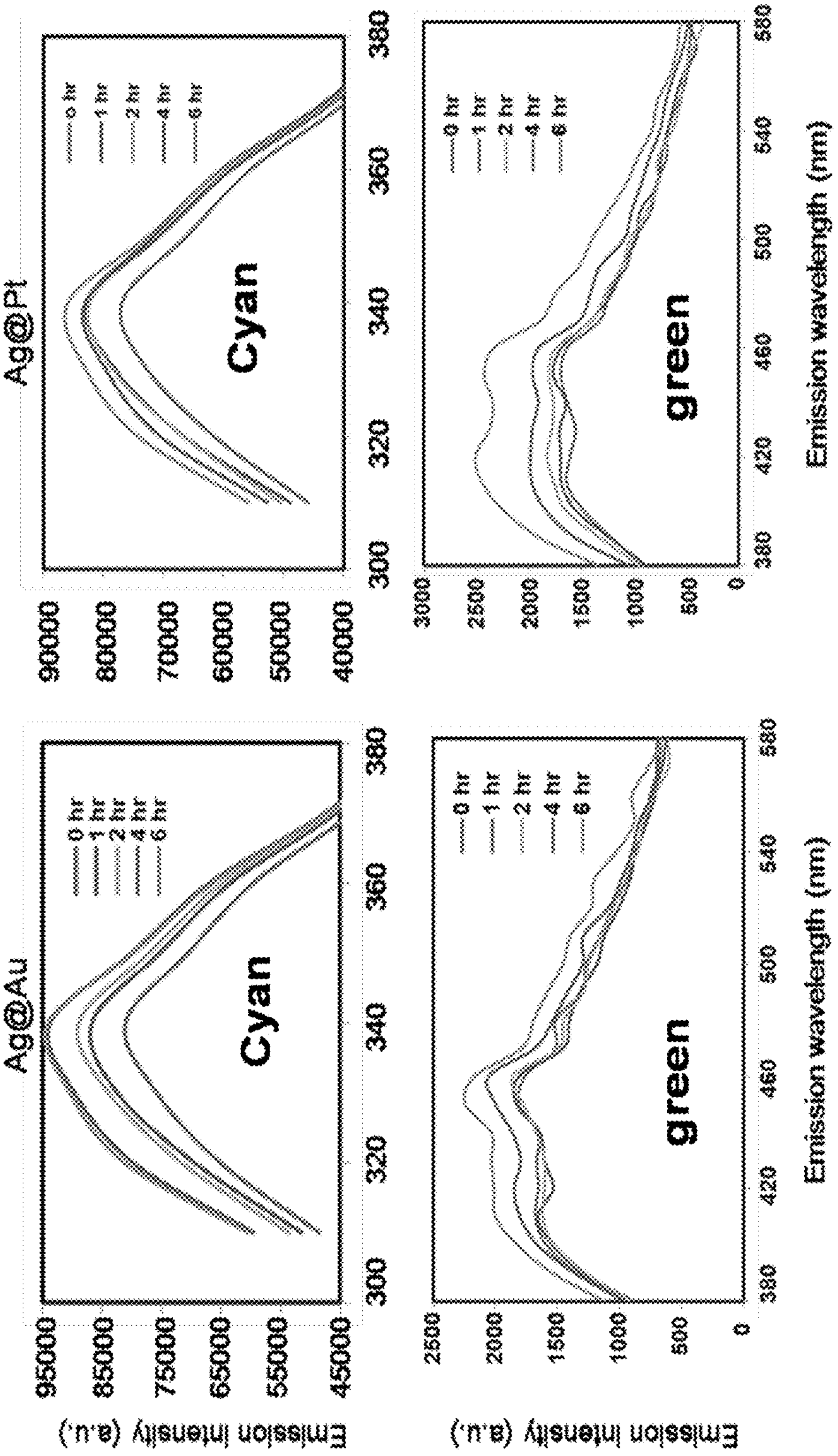
FIG. 13 represents fluorescence emission at different time points (0-6 hr) of synthesized Ag@Au and Ag@Pt NCs. The representative images show the fluorescence emission at cyan region ($\lambda_{Em}$=340 nm) for Ag@Au, Ag@Pt and in the green region ($\lambda_{Em}$=450 nm) for Ag@AuAg@Pt NCs.

TUNEL assay [Terminal deoxynucleotidyl transferase (TdT) dUTP Nick-End Labeling]: It is one of the assays to determine the apoptosis in cells caused by DNA damage. Ag@Au and Ag@PtNCs treated and untreated tumor tissues were stained using a commercial TUNEL assay k (BD Biosciences) following the manufacturers' protocol. Finally, images were captured using fluorescence microscope (Nikon Eclipse: TE 2000-E, Japan) at 20× magnification. TUNEL positivity (green fluorescence comes due to FITC) is highly detectable in tumors sections of mice treated with Ag@Au and Ag@Pt NCs. The cell nucleus was stained with DAPI, which show blue fluorescence (FIG. 12). It is evident from the result that Ag@Au and Ag@Pt NCs are more efficient for tumor therapy by an effective suppression of tumor growth.

Example 21

Spectro-fluorimetty study: Nanocomposite exhibits high fluorescence which is very useful for their different applications. The actual reason for their fluorescence is still unknown. Recent studies indicating the ligand to metal charge transfer and quantum confinement in the metal core are one of major reasons. If a nanoparticle or ligand is present in a close proximity to any plasmonic metal nanoparticle (gold, platinum etc.), owing to the coupling of nanoparticles surface plasmon with oscillating electrons system, enhancement of fluorescence emission intensity occur. Eventually, the fluorescence of Ag@Au and Ag@Pt NCs are coming due to this plasmonic enhancement, which are generated by the close proximal arrangement of silver nanoparticles with both gold (for Ag@Au NC) and platinum (for Ag@Pt NC) nanoparticles. The step by step production of the NCs with respect to time in both cyan as well as in green interface region are observed under fluorescence spectrometry. Consequently, there is no significant increase in the fluorescence observed after 6 h of time point which confirmed the formation of the Ag@Au and Ag@Pt NCs (FIG. 12). Similarly, we have also checked the fluorescence of protein lysozyme. The protein lysozyme did not show any emission in the green region of visible spectra.

Example 22

Figure 14:
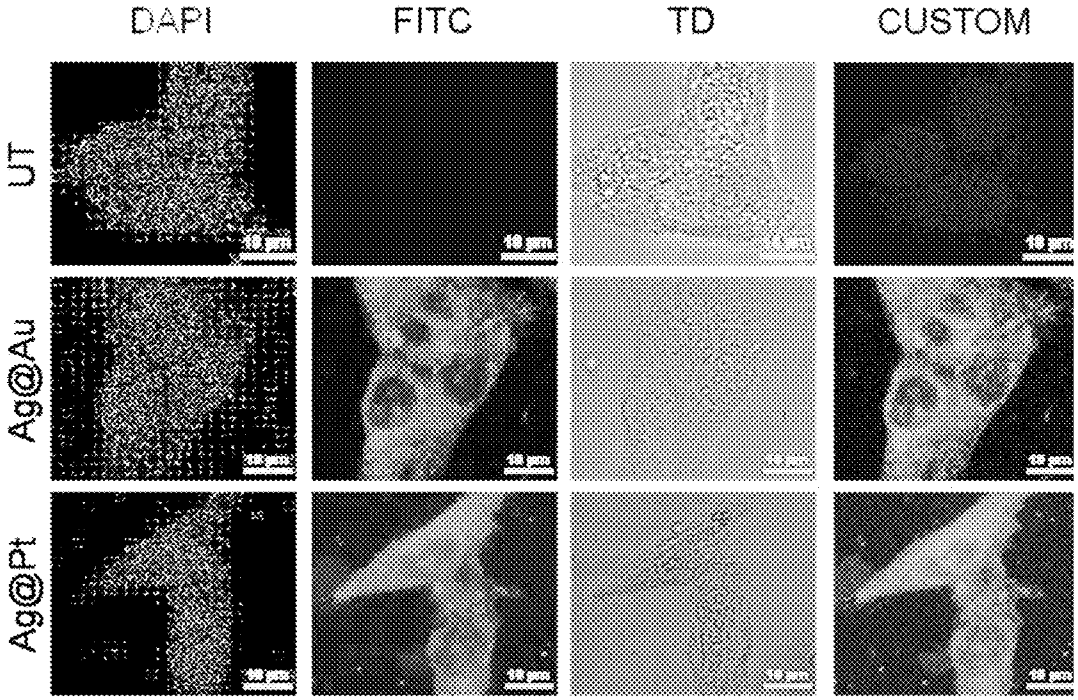
FIG. 14 represents Cell imaging study in MCF7 cell line. Confocal Microscopic pictures of UT cells (first row), treated with nothing Ag@Au [Dose: 10 μL pellet/mL of media corresponding to 0.56 μM of Ag] (second row), Ag@Pt [Dose: 10 μL pellet/mL of media corresponding to 0.51 μM of Ag] (third row) show green fluorescent inside the cell. First column from left shows the DAPI (blue field, nucleus), FITC (green fluorescent coming from the NCs), TD (phase contrast images in bright field) and fourth column shows the custom (merged images), respectively. All the pictures are taken at 40× magnification, zoom-2.303 [Nikon Ti-Eclipse, laser used, 404.2 nm, 488 nm].

Confocal microscopy study for cell imaging: In order to check the uptake of both the NCs (Ag@Au and Ag@Pt) via confocal microscopy, cancer cells (MCF-7) were grown in a 6 well cell culture dishes on embedded cover slips at a density of ~$5\times10^5$ cells/well. After 18-24 h, the cells were treated with Ag@Au and Ag@Pt NCs. After incubation for 4 h with the NCs, cells were washed thoroughly with DPBS for 3-4 times, followed by fixation with 4% paraformaldehyde (PFA) solution for 10 minutes. Further, the cells were washed with DPBS and permeabilized with 0.1% Triton X-100 in DPBS. The cells were washed with DPBS (2-3 times), mounted on DAPI vectashield on the glass plate for confocal imaging [laser used, 404.2 nm, 488 nm in Nikon TiEclipse Confocal Microscope]. Results reveal that both the NCs exhibit green fluorescence inside the cell (FIG. 14). This cell imaging capability of the NCs provide scope for future application of the NCs.

Example 23

Figure 15A:
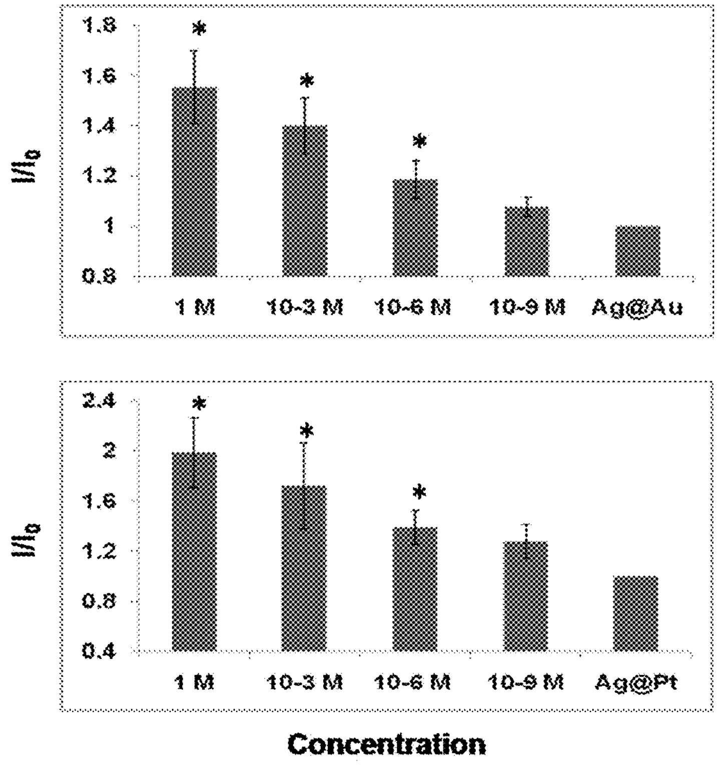
FIGS. 15A-15C represent (FIG. 15A) $H_2O_2$ sensing data outside the cells (test tube conditions) $I/I_0$ vs. concentration (M) plots show the increase in green fluorescence in presence of $H_2O_2$ for Ag@Au, Ag@Pt NCs with increasing the concentration of $H_2O_2$ [$10^{-9}$-1M]. Cellular internalized fluorescence quantification using the lysate.

$H_2O_2$ sensing in vitro condition: In order to check whether the synthesised NCs are capable of sensing hydrogen peroxide ($H_2O_2$) we have performed $H_2O_2$ sensing invitro condition. Briefly, different concentration of $H_2O_2$ solutions ($1\text{-}10^{-9}$ M) was prepared by diluting 30% w/v $H_2O_2$ using mili-Q. After that, 900 μL of respective $H_2O_2$ solution was mixed with 100 μL of the Ag@Au and Ag@Pt NCs and incubated in room temperature for 15 minutes. Thereafter, fluorescence of each solution was measured using spectrofluorimetry at green region. Only NCs solutions in water were taken as a negative control. From, the plot of $I/I_0$ vs. concentration (where, '$I_0$' denoted the fluorescence emission intensity of NC at particular wavelength and 'I' denoted the fluorescence emission intensity of NC at that wavelength after incubation with $H_2O_2$), it is evident that the $I/I_0$ value increase for both the NCs in green region of spectra (FIG. 15A).

Example 24

Figure 15B:
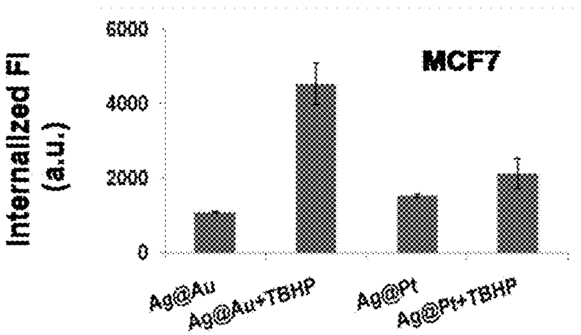
Figure 15C:
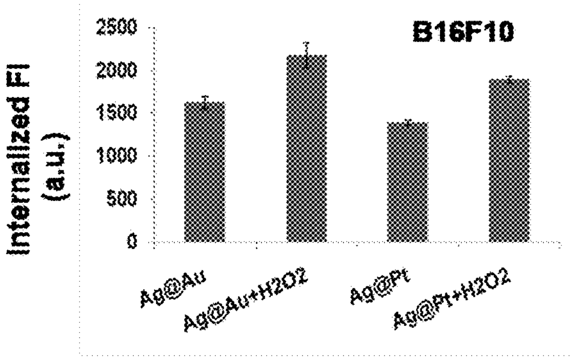

Cellular internalized fluorescence measurement in presence and absence of ROS generating agent: Cancer cell lines MCF7 and B16F10 were seeded in 6 well cell culture dishes at a density of $5\times10^4$ cells/well. The cells were grown for 24 h at 37° C. in the cell culture incubator. Both the cancer cell lines were treated with Ag@Au-NC; Ag@Pt-NC and incubated for 4 h at similar conditions. Similarly, another set of experiments were carried out after incubating the MCF7 cells with both the NCs for 4 h and with TBHP (100 μM) for another 1 h. In case of B16F10 cells, $H_2O_2$ (300 μM) was incubated for another 1 h after incubating the cells with both the NCs for 4 h. After the incubation periods, all the wells were thoroughly washed with DPBS for 2-3 times (to remove the surface attached molecules), 500 μL of RIPA buffer was then added in each well and kept for 10 minutes at 4° C. Cells lysate were collected after scratching with cell scraper and centrifugation was carried out at 14,000 rpm, 10 minutes at 4° C. using spin win centrifuge. The fluorescence of internalized compounds in two different cell lines were measured using fluorescence spectrophotometer with an excitation at $\lambda_{ex}$=380 nm and emission at $\lambda_{em}$=460 nm. Results show that there is an increase in the green fluorescence intensity in presence of TBHP (ROS generating agent) compared to naked NCs treated cells in MCF7 cell line (FIG. 15B). The internalized fluorescence (green) intensity is also measured using the B16F10 cell lysate. The cells treated with Ag@Au and Ag@Pt NCs in presence of $H_2O_2$ for 4 h showed higher intensity compared to only treated Ag@Au and Ag@Pt NCs (FIG. 15C). This data supports our hypothesis that Ag@Au and Ag@Pt NCs can act as an $H_2O_2$ sensing agent.

Example 25

Figure 16A:
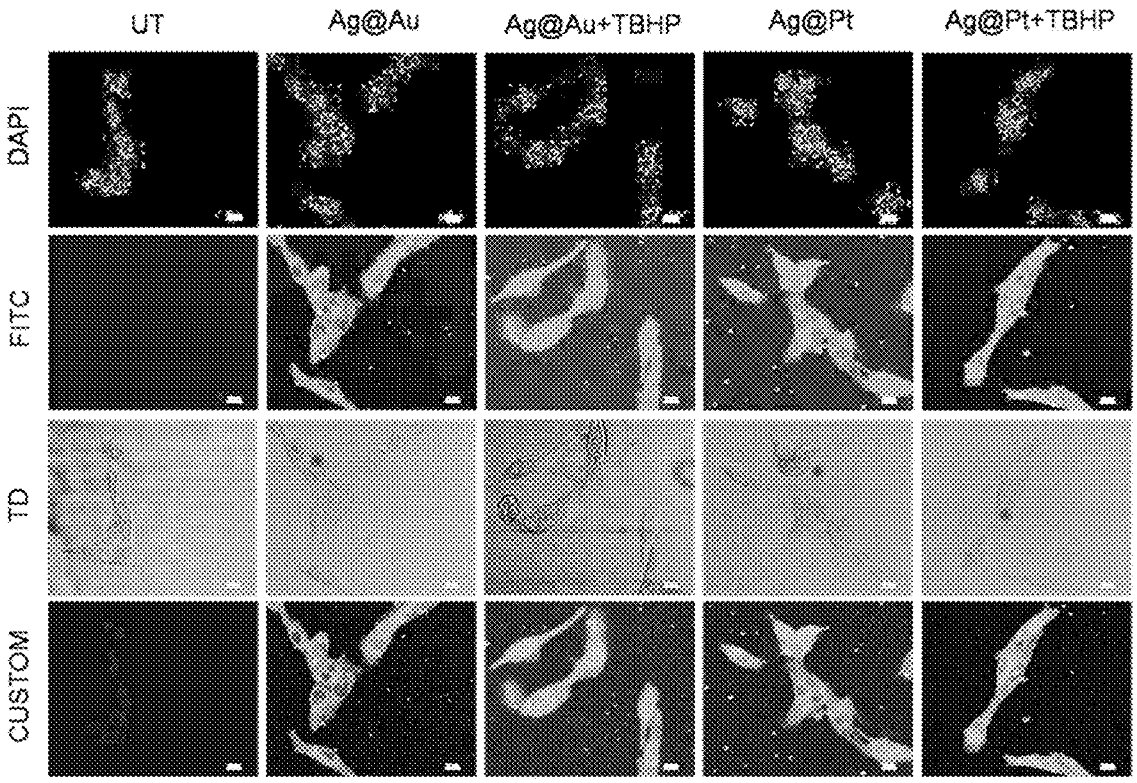
FIGS. 16A and 16B represent (FIG. 16A) In vitro sensing of $H_2O_2$ in MCF7 cell line shows increase in green fluorescence in presence of ROS inducer (mainly $H_2O_2$) TBHP (100 μM). First column indicates UT cells, second column only Ag@Au, third column Ag@Au+TBHP, fourth column only Ag@Pt and fifth column indicates Ag@Pt+TBHP treated cells. First, second, third and fourth rows show the DAPI, FITC (green field), TD (phase contrast images) and custom (merged images), respectively. All the images were captured at 40× magnification using Confocal microscopy [Nikon Ti-Eclipse, laser used, 404.2 nm, 488 nm].
Figure 16B:
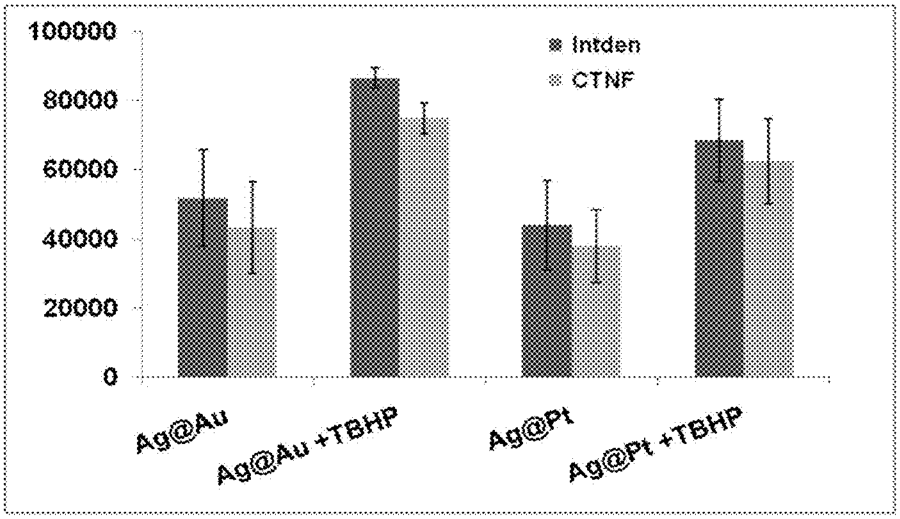

$H_2O_2$ sensing in cellular condition: Hydrogen peroxide ($H_2O_2$) is present in all aerobic species as an essential ubiquitous oxidant. In order to check whether there is an effect of the synthesized NCs in presence of the $H_2O_2$ in biological environment, we treated the MCF7 cell line with both the Ag@Au and Ag@Pt NCs for 4 h and TBHP (100 μM) was incubated for another 1 h. Briefly, MCF-7 cells were grown in a 35 mm confocal dishes at a density of ~$5\times10^5$ cells/well. The cells were treated with Ag@Au and Ag@Pt NCs after 18-24 h time points. After incubation for 4 h with the NCs, TBHP (100 μM) was incubated for another 1 h. Finally, cells were washed thoroughly with DPBS for 3-4 times. Result reveal that only NCs treated cells show less green fluorescence inside the cells compared to NCs treated cells in presence of TBHP, a ROS generating agent (FIG. 16A). These prove the $H_2O_2$ sensing ability of the nanocomposites inside the cells. The corrected total cell fluorescence (CTCF) as well as the integrated density (Intden) was quantified using the Image J software (FIG. 16B).

Example 26

Figure 17:
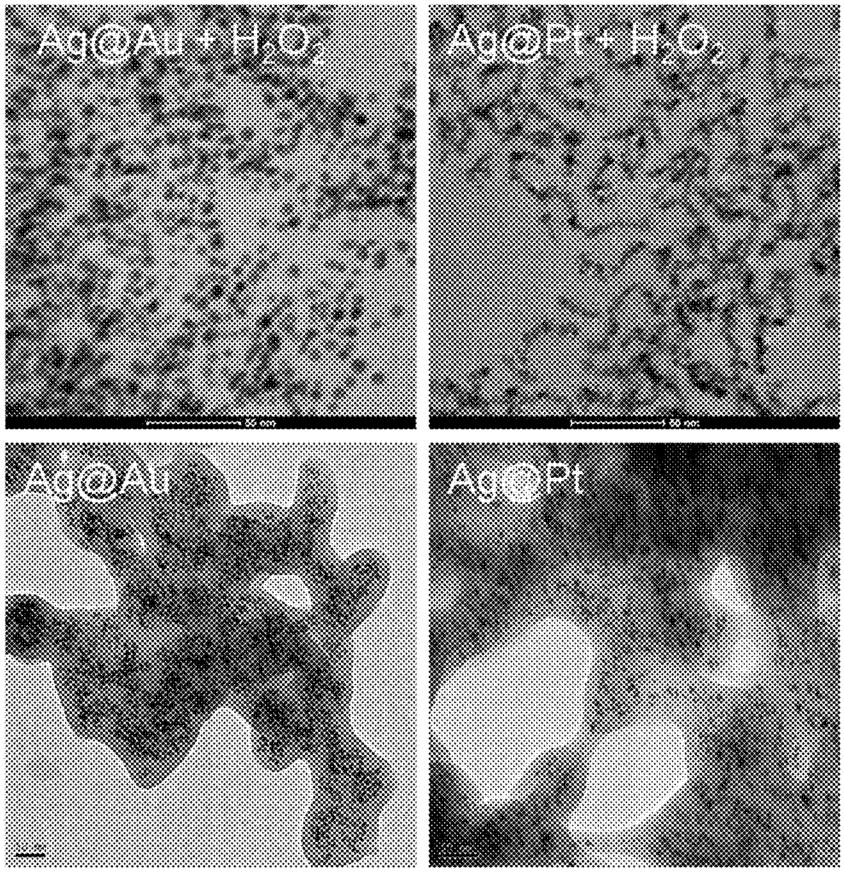
FIG. 17 represents TEM images of only Ag@Au, Ag@Au incubated with $H_2O_2$ (Ag@Au+$H_2O_2$), Ag@Pt, Ag@Pt incubated with $H_2O_2$ (Ag@Pt+$H_2O_2$) show the changes in shape of the NCs.

Shape variation of NCs after addition of $H_2O_2$: In order to check the size and shape variation of the NCs after addition of the $H_2O_2$, TEM analysis was performed. Briefly, 900 μL of $10^{-3}$ M $H_2O_2$ was added to the 100 μL of the Ag@Au and Ag@PtNCs solution. The solution mixtures were incubated for 15 min at room temperature. The solutions were then drop-casted on carbon coated copper grid and allowed to dry for overnight. From TEM images it is evident that $H_2O_2$ caused the oxidation of AgNPs into Ag+ (silver ion) that attributes to the disappearance of AgNPs coating on AuNPs/PtNPs in case of Ag@Au and Ag@Pt NCs, respectively (FIG. 17). Generally, lysozyme contains positive surface charge that gets adsorbed by negative charged AgNPs through electrostatic interactions resulting in decrease in the electronic transition between lysozyme to AuNPs or lysozyme to PtNPs. As a matter of fact, reduction in fluorescence of Ag@Au and Ag@Pt NCs observed. However, the fluorescence could be recovered and gets intensified in presence of $H_2O_2$ which attributes to oxidation of AgNPs into soluble Ag+.

Thus, the present disclosure presents a simple approach to prepare lysozyme-based biocompatible bimetallic nanocomposites having multiple applications and great potential in cancer theranostics for its use in forthcoming days. The NCs are stable in physiological environments and biocompatible towards in vitro and in vivo systems.

The NCs exhibit an escalated anti-cancer activity towards different cancer cells.

Additionally, in vitro cell imaging and $H_2O_2$ detection in cells are also demonstrated by the NCs.

Detailed mechanism studies show that the NCs could inhibit the cancer cell proliferation through multi-regulatory pathway mainly by arresting cell cycle and propagating the cell mediated death operation like apoptosis pathway.

We claim:

1. A bimetallic fluorescent nanocomposite comprising:

(i) a metal $M_1$ as an outer layer of the nanocomposite;

(ii) a metal $M_2$ as an inner metallic layer of the nanocomposite; and (iii) a capping agent, wherein:

the metal $M_1$ is selected from the group consisting of silver, chromium, manganese, iron, cobalt, nickel, copper, zinc, magnesium, and calcium;

the metal $M_2$ is a metal nanoparticle selected from the group consisting of gold, platinum, chromium, magnesium, calcium, copper, palladium, manganese, cobalt, nickel, titanium, zinc, cerium, iron, and thallium;

the capping agent is a lysozyme protein; and the lysozyme protein is a biocompatible globular protein.

2. The bimetallic fluorescent nanocomposite of claim 1, wherein the bimetallic fluorescent nanocomposite has a size from 100 nm to 300 nm and a spherical shape.

3. The bimetallic fluorescent nanocomposite of claim 1, wherein the bimetallic fluorescent nanocomposite has a lysozyme protein concentration of 10 mg/mL.

4. The bimetallic fluorescent nanocomposite of claim 1, wherein an outer framework of the bimetallic fluorescent nanocomposite is formed by the metal $M_1$ and the capping agent.

5. The bimetallic fluorescent nanocomposite of claim 1, wherein the metal $M_1$ is silver, the metal $M_2$ is gold, the bimetallic fluorescent nanocomposite is a Ag@Au nanocomposite, and a zeta potential (2) of the Ag@Au nanocomposite is −29.2 eV.

6. The bimetallic fluorescent nanocomposite of claim 1, wherein the metal $M_1$ is silver, the metal $M_2$ is platinum, the bimetallic fluorescent nanocomposite is a Ag@Pt nanocomposite, and a zeta potential (ζ) of the Ag@Pt nanocomposite is −59.2 eV.

7. The bimetallic fluorescent nanocomposite of claim 1, wherein the bimetallic fluorescent nanocomposite exhibits a green fluorescence useful for imaging of cancer cells.

8. The bimetallic fluorescent nanocomposite of claim 1, wherein the bimetallic fluorescent nanocomposite exhibits hydrogen peroxide sensing application by fluorescence enhancement property inside cells in in vitro conditions of $1\times10^{-9}$ M.

9. The bimetallic fluorescent nanocomposite of claim 1, wherein the bimetallic fluorescent nanocomposite shows cytotoxicity toward cancer cells selected from B16F10, MDA-MB-231, MCF-7, and HeLa under in vitro conditions.

10. The bimetallic fluorescent nanocomposite of claim 1, wherein the bimetallic fluorescent nanocomposite utilizes hydrogen peroxide and reactive oxygen species near a tumor microenvironment to modulate its structure to release silver ions that assist in killing cancer cells and display tumor regression in a murine melanoma in vivo model.

11. A process for preparing the bimetallic fluorescent nanocomposite according to claim 1, the process comprising:

(i) providing an aqueous solution of a salt of the metal $M_2$;

(ii) optionally adding an aqueous solution of a stabilizing agent;

(iii) adding an aqueous solution of sodium borohydride ($NaBH_4$) at a temperature from 25° C. to 35° C. under stirring to obtain a first reaction mixture comprising nanoparticles of the metal $M_2$;

(iv) adding an aqueous solution of a salt of the metal $M_1$ to the first reaction mixture obtained in (iii) at from 25° C. to 35° C. with stirring to obtain a second reaction mixture;

(v) adding an aqueous solution of a capping agent to the second reaction mixture obtained in (iv) to obtain a first solution, wherein the capping agent is a lysozyme protein;

(vi) adjusting pH of the first solution obtained in (v) to from 9 to 11 by adding an aqueous solution of sodium hydroxide (NaOH), followed by stirring for 10 minutes to 15 minutes at a temperature from 25° C. to 35° C., to obtain a second solution;

(vii) adding an aqueous solution of sodium borohydride to the second solution obtained in (vi) at from 25° C. to 35° C. for 6 hours to 8 hours with stirring to obtain a nanocomposite solution; and (viii) centrifuging the nanocomposite solution obtained in (vii) at a speed from 6000 rpm to 10,000 rpm, at a temperature from 15° C. to 20° C. for 20 minutes to 30 minutes, followed by washing with water to obtain the bimetallic fluorescent nanocomposite.

12. The process of claim 11, wherein the salt of the metal $M_1$ is selected from the group consisting of silver nitrates, chromium nitrates, manganese nitrates, iron nitrates, cobalt nitrates, nickel nitrates, copper nitrates, zinc nitrates, magnesium nitrates, and calcium nitrates.

13. The process of claim 11, wherein the salt of the metal $M_2$ is selected from the group consisting of gold chlorides, platinum chlorides, chromium chlorides, magnesium chlorides, calcium chlorides, copper chlorides, palladium chlorides, manganese chlorides, cobalt chlorides, nickel chlorides, titanium chlorides, zinc chlorides, cerium chlorides, iron chlorides, and thallium chlorides.

14. The process of claim 11, comprising adding the aqueous solution of the stabilizing agent in (ii), wherein the stabilizing agent is polyethylene glycol.

15. The bimetallic fluorescent nanocomposite of claim 1, wherein the metal $M_1$ is selected from the group consisting of silver, chromium, manganese, iron, cobalt, nickel, copper, zinc, magnesium, and calcium.

* * * * *